(12) United States Patent
MacMillan et al.

(10) Patent No.: US 7,592,463 B2
(45) Date of Patent: Sep. 22, 2009

(54) ENANTIOSELECTIVE TRANSFORMATION OF α,β-UNSATURATED KETONES USING CHIRAL ORGANIC CATALYSTS

(75) Inventors: David W. C. MacMillan, Pasadena, CA (US); Alan B. Northrup, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 437 days.

(21) Appl. No.: 10/313,744

(22) Filed: Dec. 5, 2002

(65) Prior Publication Data
US 2003/0220507 A1    Nov. 27, 2003

Related U.S. Application Data

(60) Provisional application No. 60/338,384, filed on Dec. 5, 2001.

(51) Int. Cl.
C07D 233/28    (2006.01)
C07D 235/02    (2006.01)
C07C 45/69    (2006.01)

(52) U.S. Cl. .................. 548/302.1; 548/316.4; 568/343

(58) Field of Classification Search .............. 548/302.1, 548/316.4; 568/343
See application file for complete search history.

(56) References Cited

U.S. PATENT DOCUMENTS

| | | | |
|---|---|---|---|
| 5,801,148 A | 9/1998 | Gyorkos et al. | |
| 5,859,190 A | 1/1999 | Meyer et al. | |
| 6,307,057 B1 | 10/2001 | MacMillan et al. | |
| 6,369,243 B1 | 4/2002 | MacMillan et al. | |

FOREIGN PATENT DOCUMENTS

| | | |
|---|---|---|
| WO | WO 92/02505 | 2/1992 |
| WO | WO 01/53241 | 7/2001 |

OTHER PUBLICATIONS

Vidal et al., J. Org. Chem., vol. 66, No. 24, pp. 8268-8272 (2001).*
Feenstra et al., Tetrahedron, vol. 46, No. 5, pp. 1745-1756 (1990).*
Harmon et al., J. Heterocyclic Chem., vol. 7(2), pp. 439-442 (1970).*
Shimomura et al., Nippon Kagaku Zasshi, vol. 81, pp. 1438-1439 (1960).*
Anders Kjaer, Acta Chemica Scandinavica, vol. 7, pp. 900-905 (1953).*
Shaw et al., J. Amer. Chem. Soc., vol. 71, pp. 1691-1694 (1949).*
Granacher et al., Helvetica Chimica Acta, vol. 10, pp. 819-826 (1927).*
Granacher et al., Helvetica Chimica Acta, vol. 10, pp. 815-819 (1927).*
Granacher et al., Helvetica Chimica Acta, vol. 10, pp. 246-262 (1927).*
Feenstra et al. "Oxidative Preparation of Optically Active N-Hydroxy-a-Amino Acid Amides" Tetrahedron, 1990, vol. 46, No. 5, pp. 1745-1756.*

Jen et al. "New Strategies for Organic Catalysis: The First Enantioselective Organocatalytic 1,3-Dipolar Cycloadditions Journal of the American Chemical Society" 2000, vol. 122, pp. 9874-9875.*
Ahrendt et al. (2000), "New Strategies for Organic Catalysis: The First Highly Enentioselective Organocatalytic Diels-Alder Reaction," J. Am. Chem. Soc. 122(17):4243-4244.
Jen et al. (2000), "New Strategies for Organic Catalysis: The First Enantioselective Organocatalytic 1,3-Dipolar Cycloaddition," J. Am. Chem. Soc. 122(40):9874-9875.
Paras et al. (2001), "New Strategies in Organic Catalysis: The First Enantioselective Organocatalytic Friedel-Crafts Alkylation," J. Am. Chem. Soc. 123(18):4370-4371.
Shi et al. (1995), "Synthesis of Axially Dissymmetric Chiral Ammonium Salts by Quaternization of Secondary Amines with (R)-(+)-2,2'-Bis(bromomethyl)-6,6'-Dinitrobinphenyl and (R)-(+)-2,2'-Bis(bromomethyl)-1,1'-Binaphthyl and an Examination of Their Abilities as Chiral Phase-Transfer Catalysts," J. Chem. Research (S), pp. 46-47 (J. Chem. Research (M). pp. 401-411).
Yang et al. (1998), "Design and Synthesis of Chiral Ketones for Catalytic Asymmetric Epoxidation of Unfunctionalized Olefins," J. Am. Chem. Soc. 120(24):5943-5952.
Feenstra et al. (1990), "Oxidative Preparation of Optically Active N-Hydroxsy-α-Amino Acid Amides," Tetrahedron 46(5):1745-1756.

* cited by examiner

Primary Examiner—Rei-Tsang Shiao
Assistant Examiner—Joseph R Kosack
(74) Attorney, Agent, or Firm—Isaac M. Rutenberg; Mintz, Levin, Cohn, Ferris, Glovsky, and Popeo, PC

(57) ABSTRACT

Nonmetallic organic catalysts are provided that facilitate the enantioselective reaction of α,β-unsaturated ketones. The catalysts are chiral imidazolidinone compounds having the structure of formula (IIA) or (IIB)

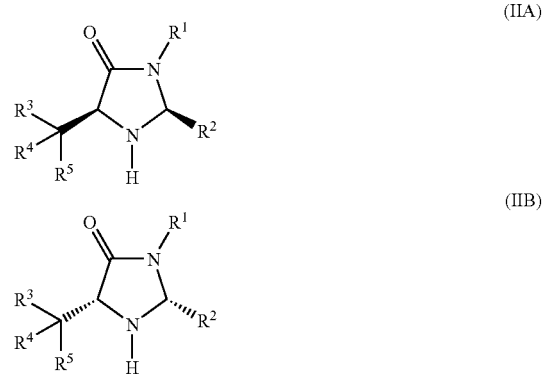

or are acid addition salts thereof, wherein, in one preferred embodiment, $R^1$ is $C_1$-$C_6$ alkyl, $R^2$ is phenyl or 2-methylfuryl, $R^3$ and $R^4$ are hydrogen, and $R^5$ is phenyl optionally substituted with 1 or 2 substituents selected from the group consisting of halo, hydroxyl, and $C_1$-$C_6$ alkyl. The chiral imidazolidinones are useful in catalyzing a wide variety of reactions, including cycloaddition reactions, Friedel-Crafts alkylation reactions, and Michael additions.

29 Claims, No Drawings

ENANTIOSELECTIVE TRANSFORMATION OF α,β-UNSATURATED KETONES USING CHIRAL ORGANIC CATALYSTS

CROSS-REFERENCE TO RELATED APPLICATIONS

This application claims priority under 35 U.S.C. §119(e)(1) to provisional U.S. patent application Ser. No. 60/338,384, filed Dec. 5, 2001. The disclosure of the aforementioned application is incorporated by reference in its entirety.

TECHNICAL FIELD

This invention relates generally to catalysis of enantioselective reactions, and more particularly relates to the use of chiral organic compounds as catalysts for a variety of reactions involving α,β-unsaturated ketones as reactants.

BACKGROUND

Ancillary (or "spectator") ligand-metal coordination complexes (e.g., organometallic complexes) and compositions are useful as catalysts, stoichiometric reagents and therapeutic agents. The ancillary ligand contains functional groups that bind to one or more metal centers and remain associated therewith, providing an opportunity to modify the steric, electronic and chemical properties of the active sites of the complex, i.e., the metal centers.

Unfortunately, many organometallic reagents are expensive and depending on their catalytic activity may not be commercially viable. Moreover, many organometallic complexes are useful only for very specific chemical reactions and do not have broad utility as catalysts for a variety of different types of reactions. This problem may be emphasized for the catalysis of reactions leading to chiral molecules, particularly the conversion of either chiral or achiral molecules via enantioselective catalysis to provide a chiral product.

Over the last 30 years enantioselective catalysis has become one of the most important frontiers in exploratory organic synthetic research. In the pharmaceutical industry and other industries, the use of pure enantiomeric molecules is often important for safety and efficacy. Thus, in the production of pharmaceuticals, use of catalysts or reagents that preferentially produce one enantiomer of a molecule relative to another enantiomer is particularly advantageous. Unfortunately, the catalysts that produce such enantiomers are typically organometallic complexes that are specific for a particular reaction. In addition, there is no way to predict with any reasonable accuracy which enantiomer will result. Examples of organometallic catalysts used to prepare chiral materials include BINOL-based complexes (Mikami et al. (1994) *J. Am. Chem. Soc.* 116:2812; Kobayashi et al. (1994) *J. Am. Chem. Soc.* 116:4083; Mikami et al. (1989) *J. Am. Chem. Soc.* 111:1940; Mikami et al. (1994) *J. Am. Chem. Soc.* 116:4077; Keck et al. (1993) *J. Am. Chem. Soc.* 115:8467; Keck et al. (1995) *J. Am. Chem. Soc.* 117:2363), BINAP-based complexes (Miyashita et al. (1980) *J. Am. Chem. Soc.* 102:7932; Miyashita et al. (1984) *Tetrahedron* 40:1245; Takaya et al. (1986) *J. Org. Chem.* 51:629; Takaya et al. (1988) *Org. Synth.* 67:20; Cai et al. (1995) *Tetrahedron Lett.* 36:7991), DUPHOS complexes (Burk et al. (1990) *Organometallics* 9:2653; Burk et al. (1993) *J. Am. Chem. Soc.* 115:10125; Burk et al. (1992) *J. Am. Chem. Soc.* 114:6266; Burk et al. (1995) *J. Am. Chem. Soc.* 117:9375); salen-based complexes (i.e., organometallic complexes containing the N,N-bis(3,5-di-t-butylsalicylidene)-1,2-cyclohexane-diamino ligand; see, e.g., Li et al. (1993) *J. Am. Chem. Soc.* 115:5326, and Evans et al. (1993) *Tetrahedron Lett.* 34:7027), and bisoxazoline-containing compounds (Evans et al. (1993) *J. Am. Chem. Soc.* 115:6460; Evans et al. (1997) *J. Am. Chem. Soc.* 119:7893; Evans et al. (1996) *Tetrahedron Lett.* 37:7481; Corey et al. (1992) *Tetrahedron Lett.* 33:6807; Gothelf et al. (1996) *J. Org. Chem.* 61:346).

Despite the observed need and relatively few, narrow solutions, relatively few asymmetric transformations have been reported which employ organic molecules as reaction catalysts. There is tremendous potential for academic, economic and environmental benefit should versatile, chiral organic catalysts be developed. Only a few researchers have disclosed organic catalysts useful for preparing chiral materials. See, e.g., *Asymmetric Catalysis in Organic Synthesis*, Noyori, R., Ed. (New York: Wiley, 1994) and *Asymmetric Synthesis*, Ojima, I., Ed. (New York: VCH, 1993), and references cited therein. Also see Yang et al. (1998) *J. Am. Chem. Soc.* 120 (24):5943-5952, who disclose the use of a dioxirane to catalyze enantioselective epoxidation, Shi et al. (1995) *J. Chem. Research (S)*:46-47 (*J. Chem. Research (M)*: 0401-0411), who disclose preparation of chiral quaternary ammonium salts stated to be useful as chiral phase-transfer catalysts by reaction of (R)-(+)-2,2-bis(bromomethyl)-6,6-dinitrobiphenyl and (R)-(+)-2,2-bis(bromomethyl)-1,1-binaphthyl with cyclic amines such as pyrrolidine, piperidine and 4-hydroxypiperidine. International Patent Publication No. WO 92/02505 to Castelijns also discloses use of a secondary amine in a catalytic transformation, i.e., in conversion of an unsaturated imine to a pyridine product, by reaction with an aldehyde or ketone.

Recently, however, certain organic catalysts have been disclosed as generally useful in a variety of enantioselective transformations, by lowering the LUMO (lowest unoccupied molecular orbital) of a reactant to facilitate reaction thereof. The organic catalysts are acid addition salts of nonmetallic compounds containing a Group 15 or Group 16 heteroatom, e.g., chiral amines, exemplified by the imidazolidinone salt (5S)-5-benzyl-2,2,3-trimethylimidazolidin-4-one hydrochloride (I)

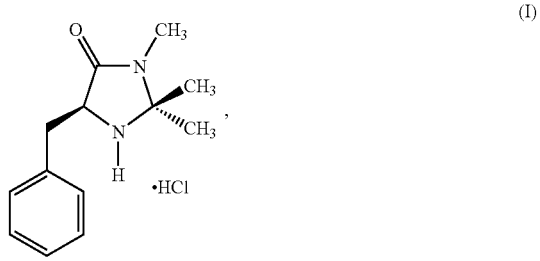

while exemplary reactants are α,β-unsaturated carbonyl compounds. Such catalysts and reactions are described in U.S. Pat. Nos. 6,307,057 to MacMillan and 6,369,243 to MacMillan et al., which disclose the utility of (I) and other chiral amine salts in catalyzing a variety of reactions, including cycloaddition reactions, 1,4 nucleophile conjugate addition reactions, 1,4 radical addition reactions, organometallic insertion reactions, and ene reactions.

The use of catalyst (I) in the LUMO-lowering activation of α,β-unsaturated aldehydes, in particular, has been reported by Ahrendt et al. (2000) *J. Am. Chem. Soc.* 122:4243-4244, Jen et al. (2000) *J. Am. Chem. Soc.* 122:9874-9875, and Paras et al. (2001) *J. Am. Chem. Soc.* 123:4370-4371. The reaction proceeds via the reversible formation of an iminium ion intermediate, which can be in one of two enantiomeric configurations. Using propenal as a reactant and (I) as the catalyst, the possible iminium ion intermediates A and B are formed (Equation 1):

Equation 1:

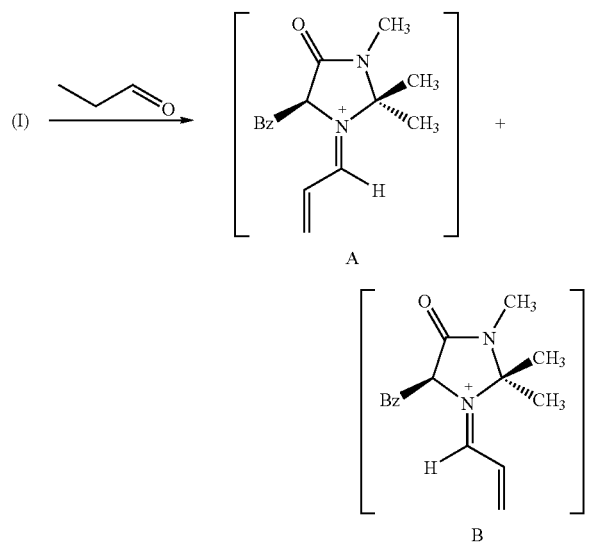

Upon further reaction, e.g., with cyclopentadiene in a Diels-Alder reaction, each intermediate results in a different enantiomeric product. That is, intermediate A gives rise to an exo product, while intermediate B results in the endo product (Equation 2):

Equation 2:

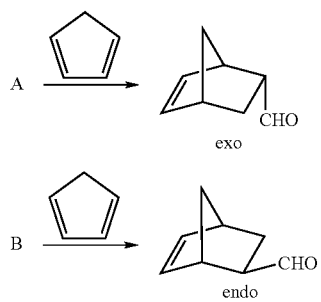

While imidazolidinone salt (I) and other chiral amines described in the foregoing references are quite valuable as enantioselective organic catalysts, they have proven to be surprisingly ineffective when α,β-unsaturated ketones are used as reactants. This is a significant limitation in the fields of organic and bioorganic synthesis because of the prevalence of enantiopure ketones in natural product architecture. Accordingly, there is a need in the art for nonmetallic catalysts that exhibit high levels of enantioselectivity and can be used with a variety of reactants. An ideal catalyst would also be inexpensive and straightforward to synthesize, compatible with aerobic and aqueous conditions, and provide for efficient reaction rates.

SUMMARY OF THE INVENTION

In one aspect of the invention, then, novel chiral catalysts are provided that address the aforementioned needs in the art, by enabling enantioselective reaction of α,β-unsaturated carbonyl compounds, particularly α,β-unsaturated ketones. The catalysts are nonmetallic, organic compounds, and thus avoid the problems associated with traditional organometallic catalysts. The present catalysts are readily synthesized from inexpensive, commercially available reagents, are generally compatible with aerobic and aqueous conditions, and provide the desired products in excellent yields with a high level of enantioselectivity. The imidazolidinones of the invention are highly effective asymmetric catalysts for a broad range of carbon-carbon bond forming reactions, and can accommodate a variety of substituents and structures in the reactant(s). The chiral catalysts are imidazolidinone compounds having the structure of formula (IIA) or (IIB)

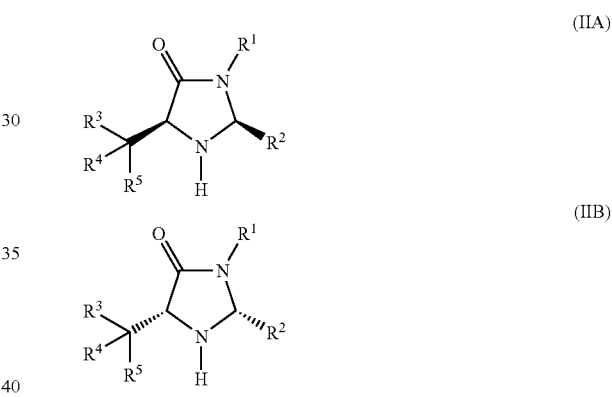

wherein:

$R^1$ is selected from the group consisting of $C_1$-$C_{12}$ hydrocarbyl, substituted $C_1$-$C_{12}$ hydrocarbyl, heteroatom-containing $C_1$-$C_{12}$ hydrocarbyl, and substituted heteroatom-containing $C_1$-$C_{12}$ hydrocarbyl;

$R^2$ and $R^5$ are independently selected from cyclic groups optionally substituted with 1 to 4 non-hydrogen substituents and containing zero to 3 heteroatoms; and $R^3$ and $R^4$ are independently selected from the group consisting of hydrogen, halo, hydroxyl, $C_1$-$C_{12}$ hydrocarbyl, substituted $C_1$-$C_{12}$ hydrocarbyl, heteroatom-containing $C_1$-$C_{12}$ hydrocarbyl, and substituted heteroatom-containing $C_1$-$C_{12}$ hydrocarbyl, and also include acid addition salts thereof.

In another aspect of the invention, a process is provided for using imidazolidinone (IIA) or (IIB) to catalyze a reaction between an α,β-unsaturated ketone and a second reactant by lowering the energy level of the lowest unoccupied molecular orbital (LUMO) of the ketone. The process involves contacting an α,β-unsaturated ketone with the second reactant in the presence of (IIA) or (IIB), either in the form of an acid addition salt, or in electronically neutral compound combined with an acid.

The α,β-unsaturated ketone has the structure of formula (III)

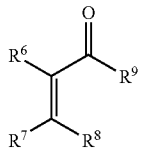

(III)

in which $R^6$, $R^7$, and $R^8$ are independently selected from the group consisting of hydrogen, $C_1$-$C_{30}$ hydrocarbyl, heteroatom-containing $C_1$-$C_{30}$ hydrocarbyl, substituted $C_1$-$C_{30}$ hydrocarbyl, substituted heteroatom-containing $C_1$-$C_{30}$ hydrocarbyl, and functional groups, and $R^9$ is —$CH_2$—$CH_2$—$R^{10}$ where $R^{10}$ is hydrogen, $C_1$-$C_{12}$ hydrocarbyl, substituted $C_1$-$C_{12}$ hydrocarbyl, heteroatom-containing $C_1$-$C_{12}$ hydrocarbyl, or substituted $C_1$-$C_{12}$ hydrocarbyl. The second reactant may be any compound that is capable of reacting with the α,β-unsaturated ketone by virtue of the lowered LUMO of the carbon-carbon double bond within the ketone in the presence of the imidazolidinone catalyst. The second reactant may or may not be covalently linked, directly or indirectly, to the first reactant, i.e., the reaction between the α,β-unsaturated ketone and the second reactant may be either intramolecular or intermolecular. Selection of the second reactant will depend on the reaction of interest; thus, for example, in a Diels-Alder reaction, i.e., a [4+2] cycloaddition reaction, the second reactant is a diene, while the first reactant, i.e., the α,β-unsaturated ketone, serves as a dienophile.

Examples of reactions that may be catalyzed using the present compounds and methods include, without limitation, cycloaddition reactions, 1,4-nucleophile conjugate addition reactions, 1,4 radical addition reactions, organometallic insertion reactions (including Heck reactions), ene reactions, and any combination thereof (including reactions occurring in tandem or cascade).

Cycloaddition reactions include, for example, [2+2] cycloaddition, [3+2] cycloaddition and [4+2] cycloaddition, with the latter reactions exemplified by Diels-Alder reactions, inverse demand Diels-Alder reactions, and hetero Diels-Alder reactions. Other types of cycloaddition reactions that can be catalyzed using the compositions and methods of the invention are described, for example, by Gothelf et al. (1998) *Chem. Rev.* 98:863-909.

1,4 Nucleophile conjugate addition reactions, include 1,4 carbon addition (e.g., cyclopropanation), 1,4 amine addition (e.g., aziridination), 1,4 oxygen addition (e.g., epoxidation), 1,4 sulfur addition, 1,4 hydride addition, and 1,4 organometallic addition. Such reactions are examples of Michael additions, wherein the second reactant is a nucleophile containing a π bond, a lone pair bearing heteroatom, or a negative charge.

In a further aspect of the invention, the chiral catalysts of the invention are used in the alkylation of nitrogen-containing heterocycles, particularly bicyclic and polycyclic compounds containing at least one N-heterocyclic ring. Such reactants include, by way of example, compounds having the structure of formula (IV)

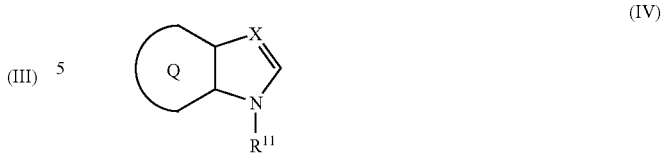

(IV)

wherein:
$R^{11}$ is selected from the group consisting of hydrogen, hydrocarbyl, substituted hydrocarbyl, heteroatom-containing hydrocarbyl, and substituted heteroatom-containing hydrocarbyl;
Q is a five- or six-membered aromatic ring containing zero to 3 heteroatoms selected from N, O and S and zero to 4 nonhydrogen substituents, wherein any two adjacent nonhydrogen substituents may together form an additional aryl, substituted aryl, heteroaryl, or heteroaryl substituent; and
X is N or $CR^{12}$ wherein $R^{12}$ is hydrogen, hydrocarbyl, substituted hydrocarbyl, heteroatom-containing hydrocarbyl, or substituted heteroatom-containing hydrocarbyl.

In one preferred embodiment of the aforementioned reaction, compound (IV) is substituted at the 3-position with a moiety -$L^1$-Nu: (i.e., X is $CR^{12}$ where $R^{12}$ is -L-Nu:) wherein $L^1$ is a hydrocarbylene, substituted hydrocarbylene, heteroatom-containing hydrocarbylene, or substituted heteroatom-containing hydrocarbylene linker with 2 to 6 atoms in the linker backbone, and Nu: is a nucleophilic group capable of addition to an unsaturated bond, e.g., secondary amino, hydroxyl, or sulfhydryl, with secondary amino groups (including —NH-Prot wherein Prot is an amine protecting group such as butyloxycarbonyl, or "BOC") most preferred. The -$L^1$-Nu: substituent enables a subsequent reaction step in which Nu: adds to the double bond of the pyrrole ring. This cycloaddition step, following the initial reaction of compound (IV) with the α,β-unsaturated ketone, enables the straightforward synthesis of a variety of polycyclic compounds, including, by way of example, pyrroloindolines, a core structure having extensive utility in the development of a wide variety of therapeutic agents.

DETAILED DESCRIPTION OF THE PREFERRED EMBODIMENTS

I. Definitions and Nomenclature:

Unless otherwise indicated, the invention is not limited to specific molecular structures, substituents, synthetic methods, reaction conditions, or the like, as such may vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a catalyst" includes a single catalyst as well as a combination or mixture of two or more catalysts, reference to "a reactant" encompasses a combination or mixture of different reactants as well as a single reactant, and the like.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used. The term "independently selected from the group consisting of" is used herein to indicate that the recited elements, e.g., R groups or the like, can be identical or different.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 18 carbon atoms, preferably 1 to about 12 carbon atoms. The term "lower alkyl" intends an alkyl group of 1 to 6 carbon atoms. "Substituted alkyl" refers to alkyl substituted with one or more substituent groups, and the terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, preferably 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, preferably 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" as used herein, and unless otherwise specified, refers to an aromatic substituent generally containing 5 to 30 carbon atoms and containing a single aromatic ring or multiple aromatic rings that are fused together, directly linked, or indirectly linked (such that the different aromatic rings are bound to a common group such as a methylene or ethylene moiety). Preferred aryl groups contain 5 to 20 carbon atoms, and particularly preferred aryl groups contain 5 to 12 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms, while preferred aralkyl and alkaryl groups contain 6 to 20 carbon atoms, and particularly preferred such groups contain 6 to 12 carbon atoms.

The term "amino" is used herein to refer to the group —$NZ^1Z^2$ wherein $Z^1$ and $Z^2$ are hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

"Hydrocarbyl" refers to univalent hydrocarbyl radicals containing 1 to about 30 carbon atoms, preferably 1 to about 24 carbon atoms, more preferably 1 to about 18 carbon atoms, most preferably about 1 to 12 carbon atoms, including linear, branched, cyclic, saturated and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—$NH_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—$NO_2$), nitroso (—NO), sulfo (—$SO_2$—OH), sulfonato (—$SO_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O$^-$)$_2$), phosphinato (—P(O)(O$^-$)), phospho (—$PO_2$), and phosphino (—$PH_2$); and the hydrocarbyl moieties $C_1$-$C_{24}$ alkyl (preferably $C_1$-$C_{18}$ alkyl, more preferably $C_1$-$C_{12}$ alkyl, most preferably $C_1$-$C_6$ alkyl), $C_2$-$C_{24}$ alkenyl (preferably $C_2$-$C_{18}$ alkenyl, more preferably $C_2$-$C_{12}$ alkenyl, most preferably $C_2$-$C_6$ alkenyl), $C_2$-$C_{24}$ alkynyl (preferably $C_2$-$C_{18}$ alkynyl, more preferably $C_2$-$C_{12}$ alkynyl, most preferably $C_2$-$C_6$ alkynyl), $C_5$-$C_{30}$ aryl (preferably $C_5$-$C_{20}$ aryl, more preferably $C_5$-$C_{12}$ aryl), and $C_6$-$C_{30}$ aralkyl (preferably $C_6$-$C_{20}$ aralkyl, more preferably $C_6$-$C_{12}$ aralkyl). In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl and aryl" is to be interpreted as "substituted alkyl and aryl." Analogous terminology is to be interpreted in the same manner.

The terms "LUMO" and "HOMO" (abbreviations for lowest unoccupied molecular orbital and highest occupied molecular orbital, respectively) refer to the frontier orbitals of two reactants (such as a diene and dienophile, in a Diels-Alder reaction), with the LUMO referring to the vacant orbital of lowest energy, in a first reactant (i.e., in an α,β-unsaturated ketone as described herein), and the HOMO referring to the orbital containing electrons of highest energy, in a second reactant.

The term "chiral" refers to a structure that does not have an improper rotation axis ($S_n$), i.e., it belongs to point group $C_n$ or $D_n$. Such molecules are thus chiral with respect to an axis, plane or center of asymmetry. Preferred "chiral" molecules herein are in enantiomerically pure form, such that a particular chiral molecule represents at least about 95 wt. % of the composition in which it is contained, more preferably at least about 99 wt. % of that composition.

The term "enantioselective" refers to a chemical reaction that preferentially results in one enantiomer relative to a second enantiomer, i.e., gives rise to a product of which a desired enantiomer represents at least about 50 wt. %. Preferably, in the enantioselective reactions herein, the desired enantiomer represents at least about 85 wt. % of the product, optimally at least about 95 wt. % of the product.

In the molecular structures herein, the use of bold and dashed lines to denote particular conformation of groups follows the IUPAC convention. A bond indicated by a broken line indicates that the group in question is below the general plane of the molecule as drawn (the "α" configuration), and a bond indicated by a bold line indicates that the group at the position in question is above the general plane of the molecule as drawn (the "β" configuration).

II. The Novel Catalysts

In one embodiment, then, chiral imidazolidinone compounds are provided for catalyzing an enantioselective reaction of an α,β-unsaturated ketone by lowering the LUMO of the carbon-carbon double bond within the ketone. The reaction will generally involve a second reactant that is capable of undergoing reaction with the activated α,β-unsaturated ketone, but the invention additionally encompasses intramolecular reactions as well, wherein the second "reactant" is directly or indirectly bound to the ketone.

The chiral imidazolidinone compounds have the structure of formula (IIA) or (IIB)

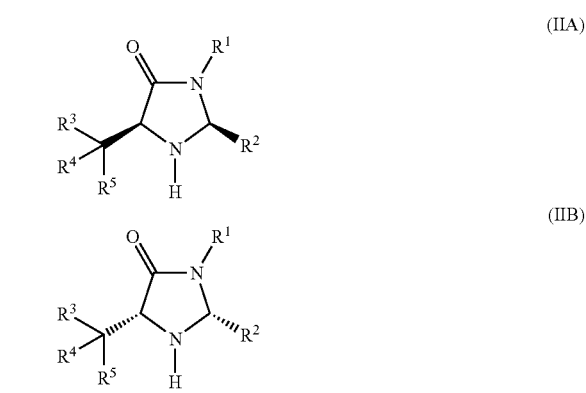

and may be in the form of an acid addition salt. In the reactions described herein, the catalyst used is either an acid addition salt of compound (IIA) or (IIB), or an acid is added to the reaction mixture to serve as a co-catalyst for compound (IIA) or (IIB) in electronically neutral form. Preferably, the catalyst is used in the form of an acid addition salt.

In formulae (IIA) and (IIB), the various substituents are as follows:

$R^1$ is selected from the group consisting of $C_1$-$C_{12}$ hydrocarbyl (e.g., alkyl, alkenyl, alkynyl, aryl, alkaryl, aralkyl, etc.), substituted $C_1$-$C_{12}$ hydrocarbyl (e.g., substituted alkyl, alkenyl, alkynyl, aryl, alkaryl, aralkyl, etc.), heteroatom-containing $C_1$-$C_{12}$ hydrocarbyl (e.g., heteroatom-containing alkyl, alkenyl, alkynyl, aryl, alkaryl, aralkyl, etc.), and substituted heteroatom-containing $C_1$-$C_{12}$ hydrocarbyl (e.g., substituted heteroatom-containing alkyl, alkenyl, alkynyl, aryl, alkaryl, aralkyl, etc.). Preferred $R^1$ substituents are $C_1$-$C_{12}$ hydrocarbyl such as $C_1$-$C_{12}$ alkyl, with $C_1$-$C_6$ alkyl groups more preferred, and $C_1$-$C_3$ alkyl groups (e.g., methyl) particularly preferred.

$R^2$ and $R^5$ are independently selected from cyclic groups optionally substituted with 1 to 4 non-hydrogen substituents and containing zero to 3 heteroatoms generally selected from N, O, and S. Preferably, $R^2$ and $R^5$ are independently selected from the group consisting of $C_5$-$C_{30}$ aryl, substituted $C_5$-$C_{30}$ aryl, $C_5$-$C_{30}$ heteroaryl, and substituted $C_5$-$C_{30}$ heteroaryl, and, more preferably, are selected from monocyclic aryl and heteroaryl Optionally substituted with 1 to 4 substituents selected from the group consisting of halo, hydroxyl, and $C_1$-$C_{12}$ hydrocarbyl. Most preferably, $R^2$ is selected from phenyl, phenyl substituted with 1 or 2 substituents selected from the group consisting of halo, hydroxyl, and $C_1$-$C_6$ alkyl, and $R^5$ is selected from phenyl and phenyl substituted with 1 or 2 substituents selected from the group consisting of halo, hydroxyl, and $C_1$-$C_6$ alkyl. Optimally, $R^2$ is phenyl or 5-methylfuryl, preferably 5-methylfuryl, and $R^5$ is phenyl.

$R^3$ and $R^4$ are independently selected from the group consisting of hydrogen, halo, hydroxyl, $C_1$-$C_{12}$ hydrocarbyl, substituted $C_1$-$C_{12}$ hydrocarbyl, heteroatom-containing $C_1$-$C_{12}$ hydrocarbyl, and substituted heteroatom-containing $C_1$-$C_{12}$ hydrocarbyl. Preferably, $R^3$ and $R^4$ are hydrogen or $C_1$-$C_{12}$ hydrocarbyl, and, optimally, $R^3$ and $R^4$ are both hydrogen.

The acid used to form the imidazolidinone salt or employed as a co-catalyst for the electronically neutral compound is generally a Bronsted acid. Suitable Bronsted acids are generally although not necessarily generally although not necessarily selected from acids having a pKa of less than about 5.

Combinations of Bronsted acids may also be used. Suitable acids include both organic and inorganic acids, with inorganic acids including, but not limited to, hydrochloric acid, hydrobromic acid, sulfuric acid, sulfurous acid, nitric acid, nitrous acid, perchloric acid, phosphoric acid, and chromic acid, and with organic acids exemplified by carboxylic acids, sulfonic acids, phosphonic acids, and aromatic alcohols, e.g., phenols, substituted with 1 to 5 electron-withdrawing substituents such as nitro, cyano, sulfonato, halo (i.e., Cl, F, Br or I) and halogenated alkyl (typically fluorinated alkyl, preferably perfluorinated lower alkyl such as trifluoromethyl). Particularly suitable organic acids are carboxylic acids and sulfonic acids having the structural formulas $R^x$—COOH and $R^x$—$SO_2$—OH wherein $R^x$ is aryl, alkyl, substituted aryl (e.g., halogenated aryl), or substituted alkyl (e.g., halogenated alkyl, particularly fluorinated and chlorinated alkyl). Preferred $R^x$ groups are methyl, halogenated methyl (e.g., fluorinated methyl such as trifluoromethyl, chlorinated methyl such as chloromethyl, dichloromethyl, and trichloromethyl, etc.), and nitrite-substituted methyl. Specific examples of preferred organic acids include acetic acid, propionic acid, glycolic acid, pyruvic acid, oxalic acid, malic acid, malonic acid, succinic acid, maleic acid, fumaric acid, tartaric acid, citric acid, benzoic acid, 2-nitrobenzoic acid, cinnamic acid, mandelic acid, methanesulfonic acid, ethanesulfonic acid, triflic acid, p-toluene sulfonic acid, salicylic acid, chloroacetic acid, dichloroacetic acid, trichloroacetic acid, trifluoroacetic acid, and combinations thereof. The Bronsted acid may or may not be chiral, and those Bronsted acids that are chiral may be used in isomerically pure form or as a racemic mixture.

Acid addition salts of the imidazolidinone may be synthesized by admixing the imidazolidinone (in uncharged, free base form) with a Bronsted acid HX, at a desired molar ratio, generally in the range of approximately 1:100 to 100:1, typically about 1:10 to 10:1, preferably about 1:2 to 2:1. Alternatively, the uncharged imidazolidinone may be combined with at least one salt $M^{q+}$ q($X^-$), thereby forming the desired imidazolidinone salt via ion exchange. A wide variety of salts may be used for this latter purpose, and the cation $M^{+q}$ can be virtually any cation, although q is generally 1, 2 or 3. Suitable M elements are typically chosen from Groups 2 to 13 of the Periodic Table of the Elements, but M may also be a polyatomic cation such as the ammonium ion $NH_4^+$. It should also be noted that the imidazolidinone salt can be prepared with two or more different Bronsted acids or metal salts, thereby forming a mixture of imidazolidinone salts, i.e., salts containing different anions $X^-$.

For purposes of exemplification, detailed descriptions of suitable methods for synthesizing catalysts of the invention are set forth in Examples 1-3.

III. Reactions

In another embodiment, a process is provided for using imidazolidinone (IIA) or (IIB) to catalyze a reaction between an α,β-unsaturated ketone and a second reactant by lowering the energy level of the lowest unoccupied molecular orbital (LUMO) of the ketone. The second reactant is one that is capable of reacting with the ketone by virtue of the lowered LUMO of the ketone in the presence of the catalyst.

The process involves contacting an α,β-unsaturated ketone with the second reactant in the presence of a catalyst composed of imidazolidinone (IIA) or (IIB), either in the form of an acid addition salt as described in the preceding section, or in the form of an electronically neutral compound combined with a Bronsted acid (an acid addition salt of the imidazolidinone may also be combined with excess imidazolidinone in electronically neutral form to tune the reaction, i.e., improving catalytic activity, conversion or selectivity), wherein the molar ratio of the imidazolidinone to the anionic counterion of the acid can be as high as about 100:1, although typically not exceeding about 20:1, and most typically not exceeding about 2:1.

The α,β-unsaturated ketone has the structure of formula (III)

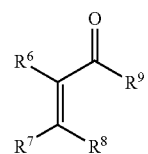

(III)

in which $R^6$, $R^7$, and $R^8$ are independently selected from the group consisting of hydrogen, $C_1$-$C_{30}$ hydrocarbyl, heteroatom-containing $C_1$-$C_{30}$ hydrocarbyl, substituted $C_1$-$C_{30}$ hydrocarbyl, substituted heteroatom-containing $C_1$-$C_{30}$ hydrocarbyl, and functional groups. In a preferred embodiment, $R^6$, $R^7$, and $R^8$ are independently selected from the group consisting of hydrogen, $C_1$-$C_{24}$ alkyl, $C_2$-$C_{24}$ alkenyl, $C_2$-$C_{24}$ alkynyl, $C_1$-$C_{24}$ alkoxy, $C_2$-$C_{24}$ alkenyloxy, $C_2$-$C_{24}$ alkynyloxy, $C_5$-$C_{30}$ aryl, $C_5$-$C_{30}$ aryloxy, $C_2$-$C_{24}$ alkoxyalkyl, $C_6$-$C_{30}$ aryloxyalkyl, hydroxyl, sulfhydryl, $C_2$-$C_{24}$ alkylcarbonyl, $C_6$-$C_{30}$ arylcarbonyl, $C_2$-$C_{24}$ alkoxycarbonyl, $C_6$-$C_{30}$ aryloxycarbonyl, halocarbonyl, $C_2$-$C_{24}$ alkylcarbonato, $C_6$-$C_{30}$ arylcarbonato, carboxy, carboxylato, carbamoyl, mono- and di-($C_1$-$C_{24}$ alkyl)-substituted carbamoyl, mono- and di-($C_5$-$C_{20}$ aryl)-substituted carbamoyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{30}$ arylamido, imino, $C_2$-$C_{24}$ alkylimino, $C_6$-$C_{30}$ arylimino, nitro, nitroso, sulfo, sulfonato, $C_1$-$C_{24}$ alkylsulfanyl, $C_5$-$C_{30}$ arylsulfanyl, $C_1$-$C_{24}$ alkylsulfinyl, $C_5$-$C_{30}$ arylsulfinyl, $C_1$-$C_{24}$ alkylsulfonyl, $C_5$-$C_{30}$ arylsulfonyl, phosphono, phosphonato, phosphinato, phospho, phosphino, and combinations thereof. In addition, any two of $R^6$, $R^7$, and $R^8$ taken together can form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms. $R^9$ is —$CH_2$—$CH_2$—$R^{10}$ where $R^{10}$ is hydrogen, $C_1$-$C_{12}$ hydrocarbyl, substituted $C_1$-$C_{12}$ hydrocarbyl, heteroatom-containing $C_1$-$C_{12}$ hydrocarbyl, or substituted $C_1$-$C_{12}$ hydrocarbyl.

In an exemplary embodiment, $R^6$ and $R^8$ are hydrogen, $R^7$ is selected from hydrogen, $C_1$-$C_{12}$ alkyl, $C_1$-$C_{12}$ alkoxy, $C_5$-$C_{20}$ aryl, $C_2$-$C_{12}$ alkoxyalkyl, and $C_6$-$C_{20}$ aryloxyalkyl, and $R^{10}$ is hydrogen, $C_1$-$C_6$ alkyl, or substituted $C_1$-$C_6$ alkyl. Preferably, $R^7$ is hydrogen, $C_1$-$C_6$ alkyl, $C_5$-$C_{12}$ aryl, or $C_6$-$C_{12}$ aryloxyalkyl, and $R^{10}$ is hydrogen, methyl, ethyl, or n-propyl.

The second reactant, as indicated above, may be any compound that is capable of reacting with the α,β-unsaturated ketone by virtue of the lowered LUMO of the carbon-carbon double bond within the ketone in the presence of the imidazolidinone catalyst. The second reactant may or may not be covalently linked, directly or indirectly, to the first reactant, i.e., the reaction between the first and second reactants may be either intramolecular or intermolecular. Examples of various reactants and corresponding reaction types are discussed in further detail below. With reactants that are not air-sensitive, the reactions can be carried out under aerobic conditions, and as the catalysts are stable under aqueous conditions, the reactions can typically be carried out in aqueous media.

Examples of reactions that may be catalyzed using the present compounds and methods include, without limitation, cycloaddition reactions, 1,4-nucleophile conjugate addition reactions, 1,4 radical addition reactions, organometallic insertion reactions (including Heck reactions), ene reactions, and any combination thereof, including reactions occurring in tandem or cascade.

Cycloaddition reactions include, for example, [2+2] cycloaddition, [3+2] cycloaddition and [4+2] cycloaddition, with the latter reactions exemplified by Diels-Alder reactions, inverse demand Diels-Alder reactions, and hetero Diels-Alder reactions. Other types of cycloaddition reactions that can be catalyzed using the compositions and methods of the invention are described, for example, by Gothelf et al. (1998) Chem. Rev. 98:863-909.

1,4 Nucleophile conjugate addition reactions, include 1,4 carbon addition (e.g., cyclopropanation), 1,4 amine addition (e.g., aziridination), 1,4 oxygen addition (e.g., epoxidation), 1,4 sulfur addition, 1,4 hydride addition, and 1,4 organometallic addition. Such reactions are examples of Michael additions, wherein the second reactant is a nucleophile containing a π bond, a lone pair bearing heteroatom, or a negative charge.

The catalysts of the invention can also serve as enantioselective Friedel-Crafts alkylation catalysts. Significantly, the novel imidazolidinones of the invention can facilitate the conjugate addition of electron-rich benzene systems to generate enantioenriched benzylic stereogenicity, an important chiral synthon for the preparation of natural products (a 2001 survey of the Beilstein database documents over 5000 naturally occurring structures that exhibit benzylic stereogenicity) as well as synthetic medicinal agents. The latter include, by way of example, sertraline (Zoloft®), tolteridine (Detrol®), and paroxetine (Paxil®), relevant syntheses of which are described by McRae et al. (2001) Expert Opin. Pharm. 2:883-892, Hills et al. (1998) Drugs 55:813-820, and Heydorn (1999) Expert Opin. Invest. Drugs 8:417-441, respectively.

Of particular interest is the use of the present catalysts and methods in the alkylation of bicyclic and polycyclic compounds containing at least one N-heterocyclic ring, as indicated above with respect to the alkylation of indoles. In this embodiment, the bicyclic or polycyclic compound, such as (IV)

(IV)

undergoes reaction with the α,β-unsaturated ketone in the presence of a catalyst of the invention i.e., having the structure of formula (IIA) or (IIB). In formula (IV):

R is selected from the group consisting of hydrogen, hydrocarbyl, substituted hydrocarbyl, heteroatom-containing hydrocarbyl, and substituted heteroatom-containing hydrocarbyl, and is preferably selected from the group consisting of hydrogen, $C_1$-$C_{12}$ alkyl, $C_1$-$C_{12}$ alkenyl, $C_5$-$C_{20}$ aryl, and $C_5$-$C_{20}$ aralkyl.

Q is a five- or six-membered aromatic ring containing zero to 3 heteroatoms selected from N, O and S and zero to 4 nonhydrogen substituents, wherein any two adjacent nonhydrogen substituents may together form an additional aryl, substituted aryl, heteroaryl, or heteroaryl substituent. In a preferred embodiment, Q is phenyl substituted with zero to 2 nonhydrogen substituents selected from the group consisting of $C_1$-$C_{12}$ alkyl, $C_1$-$C_{12}$ alkoxy, and halo.

X is N or $CR^{12}$ wherein $R^{12}$ is hydrogen, hydrocarbyl, substituted hydrocarbyl, heteroatom-containing hydrocarbyl, or substituted heteroatom-containing hydrocarbyl. Preferably, X is $CR^{12}$.

For example, the aforementioned method may involve the enantioselective alkylation of an indole at the 3-position thereof, wherein (a) an indole reactant selected from the group consisting of unsubstituted indole and indole substituted at the 1-, 4-, 5-, 6-, and/or 7-positions with a nonhydrogen substituent, is contacted with (b) an α,β-unsaturated ketone in the presence of (c) a catalyst of the invention. If the indole reactant is substituted, preferred such reactants are substituted at the 1-position (i.e., at the nitrogen of the pyrrole ring) with $C_1$-$C_{12}$ alkyl, $C_1$-$C_{12}$ alkenyl, $C_5$-$C_{20}$ aryl, or $C_5$-$C_{20}$ aralkyl, and/or substituted at the 4-, 5-, 6- and/or 7-positions with a $C_1$-$C_{12}$ alkyl, $C_1$-$C_{12}$ alkoxy, or halo substituent. Preferred indole reactants have the structure of formula (V)

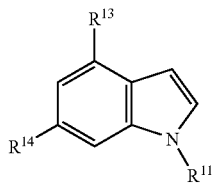
(V)

wherein: $R^{11}$ is as defined previously, and is preferably selected from the group consisting of hydrogen, $C_1$-$C_{12}$ alkyl, $C_1$-$C_{12}$ alkenyl, $C_5$-$C_{20}$ aryl, and $C_5$-$C_{20}$ aralkyl; and $R^{13}$ and $R^{14}$ are independently selected from the group consisting of hydrogen, $C_1$-$C_{12}$ alkyl, $C_1$-$C_{12}$ alkoxy, and halo. In a specific and particularly preferred embodiment, X of the bicyclic or polycyclic compound (IV) undergoing an alkylation reaction with the α,β-unsaturated ketone is $CR^{12}$ wherein $R^{12}$ is -$L^1$-Nu:, in which $L^1$ is a hydrocarbylene, substituted hydrocarbylene, heteroatom-containing hydrocarbylene, or substituted heteroatom-containing hydrocarbylene linker with 2 to 6 atoms in the linker backbone, and Nu: is a nucleophilic group capable of addition to an unsaturated bond, e.g., secondary amino, hydroxyl, or sulfhydryl, with secondary amino groups (including —NH-Prot wherein Prot is an amine protecting group such as butyloxycarbonyl, or "BOC") most preferred. Generally, $L^1$ is substituted or unsubstituted $C_2$-$C_6$ alkylene, and more preferably is $C_2$-$C_4$ alkylene (e.g., ethylene). The -$L^1$-Nu: substituent allows for a subsequent reaction step in which Nu: adds to the double bond of the pyrrole ring. This cycloaddition step, following the initial reaction of compound (IV) with the α,β-unsaturated ketone, enables the straightforward synthesis of a host of useful polycyclic compounds. Such polycyclic compounds include, by way of example, pyrroloindolines.

Accordingly, in a further embodiment, the invention pertains to a method for synthesizing a pyrroloindoline having the structure of formula (VII)

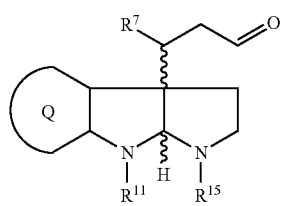
(VII)

wherein $R^7$ is selected from the group consisting of hydrogen, $C_1$-$C_{30}$ hydrocarbyl, heteroatom-containing $C_1$-$C_{30}$ hydrocarbyl, substituted $C_1$-$C_{30}$ hydrocarbyl, substituted heteroatom-containing $C_1$-$C_{30}$ hydrocarbyl, and functional groups, $R^{11}$ and Q are as defined previously, and $R^{15}$ is hydrocarbyl, substituted hydrocarbyl, heteroatom-containing hydrocarbyl, or substituted heteroatom-containing hydrocarbyl. The method involves contacting a reactant having the structure of formula (VIII)

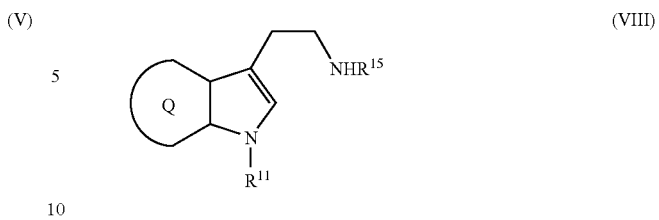
(VIII)

with an α,β-unsaturated ketone having the structure (IX)

(IX)

in the presence of a catalyst of the invention, i.e., a compound having the structure of formula (IIA) or (IIB). When the catalyst has the structure of formula (IIA), the pyrroloindoline product will have the structure of formula (VIIA)

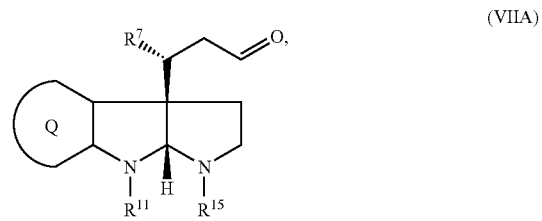
(VIIA)

while when the catalyst has the structure of formula (IIB), the pyrroloindoline product will have the structure of formula (VIIB)

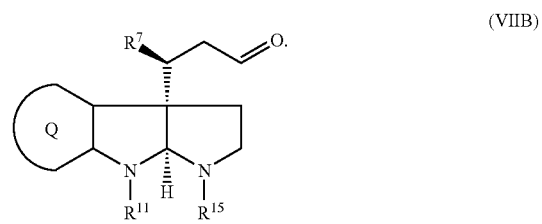
(VIIB)

The foregoing reactions are intended to be illustrative and not in any way limiting of the reactions with which the present catalysts and methods are useful. That is, the imidazolidinones of the invention are useful to catalyze a host of reactions and reaction types, of which those disclosed herein are merely representative.

Any of the reactions herein, including both preparation and use of the imidazolidinone salt, can be carried out on a solid support, using solid phase synthesis techniques. Solid-phase synthesis enables synthesis and use of the imidazolidinone salt in combinatorial chemistry processes, wherein an array or "matrix" of reactions are conducted in parallel on a single substrate. In such a case, the imidazolidinone itself (or the anion with which the cationic imidazolidinone is associated)

can be bound either directly or indirectly to the surface of a solid substrate, if indirectly, through a cleavable or noncleavable linker. For example, the imidazolidinone can be linked to the surface of a substrate through any of $R^1$ through $R^5$. Any solid support may be used. Typical substrates are those conventionally used in solid phase chemistry and which allow for chemical synthesis thereon. The only limitation upon the materials useful for constructing substrates is that they must be compatible with the reaction conditions to which they are exposed. Suitable substrates useful in practicing the methods of the invention include, but are not limited to, organic and inorganic polymers (e.g., polyethylene, polypropylene, polystyrene, polytetrafluoroethylene), metal oxides (e.g., silica, alumina), mixed metal oxides, metal halides (e.g., magnesium chloride), minerals, quartz, zeolites, and the like. Other substrate materials will be apparent to those of skill in the art.

Process conditions: The catalytic reactions of the invention are preferably although not necessarily carried out in water, organic solvents or ionic liquids, i.e., in any solvent that allows retention and regeneration of the catalyst composition and removal of the reaction product following completion of the reaction. The reactions may be carried out in batch, semi-continuously or continuously, in air or an inert atmosphere, at autogenous pressure or higher, depending, for example, on the nature of the catalyst composition and reactants used. The reaction temperature will generally be in the range of about −100° C. to 100° C., preferably in the range of about −90° C. to 50° C. The amount of catalyst (i.e., either an acid addition salt of the imidazolidinone, or a mixture of the imidazolidinone and an acid co-catalyst) is generally in the range of 1 mole % to 1 stoichiometric equivalent, and the molar ratio of the α,β-unsaturated ketone to the second reactant is generally in the range of about 100:1 to 1:100, preferably in the range of about 10:1 to 1:10. Industrially, the reaction may be scaled up to 10,000 gallons or more. Catalysis may be heterogeneous or homogeneous. It will be appreciated by those skilled in the art of catalysis that the aforementioned process conditions may vary depending on the particular reaction, the desired product, the equipment used, and the like. Generally, the reaction product is obtained after completion of the reaction, wherein an optional extraction and/or catalyst recovery step and/or drying is followed by concentration or distillation to give the crude product and purification, e.g., by chromatography, sublimation, precipitation, extraction, crystallization with optional seeding and/or co-crystallization aids. For many reactions, the catalyst can be recovered in at least an 80-90% yield. In the Diels-Alder reaction of Example 13, for example, the catalyst was recovered in 91% yield.

It is to be understood that while the invention has been described in conjunction with the preferred specific embodiments thereof, that the description above as well as the examples that follow are intended to illustrate and not limit the scope of the invention. Other aspects, advantages and modifications within the scope of the invention will be apparent to those skilled in the art to which the invention pertains.

All patents, patent applications, journal articles and other reference cited herein are incorporated by reference in their entireties.

Experimental:

In the following examples, efforts have been made to ensure accuracy with respect to numbers used (e.g., amounts, temperature, etc.) but some experimental error and deviation should be accounted for. Unless indicated otherwise, temperature is in degrees C and pressure is at or near atmospheric.

Commercial reagents were purified prior to use following the guidelines of Perrin and Armarego, *Purification of Laboratory Chemicals*, Fourth Edition (Oxford, Butterworth-Heinemann, 1996). Organic solutions were concentrated under reduced pressure on a Buichi rotary evaporator. Chromatographic purification of products was accomplished using forced-flow chromatography on ICN 60 32-64 mesh silica gel 63 according to the method of Still et al. (1978) *J. Org. Chem.* 43:2923. Thin-layer chromatography (TLC) was performed on EM Reagents 0.25 mm silica gel 60-F plates. Visualization of the developed chromatogram was performed by fluorescence quenching or $KMnO_4$.

$^1H$ and $^{13}C$ NMR spectra were recorded on Varian Mercury 300 spectrometers (300 MHz and 75 MHz respectively) as noted, and are internally referenced to residual protio solvent signals. Data for $^1H$ NMR are reported as follows: chemical shift (δ ppm), multiplicity (s=singlet, d=doublet, t=triplet, q=quartet, m=multiplet, br=broad), coupling constant (Hz), integration and assignment. Data for $^{13}C$ NMR are reported in terms of chemical shift (ppm). IR spectra were recorded on a Perkin Elmer Paragon 1000 spectrometer and are reported in terms of frequency of absorption ($cm^{-1}$). Mass spectra were obtained from the UC Irvine Mass Spectral facility. Gas liquid chromatography (GLC) was performed on Hewlett-Packard 6850 and 6890 Series gas chromatographs equipped with a split-mode capillary injection system and flame ionization detectors using ASTEC Chiraldex Γ-TA (30 m×0.25 mm) or Ǝ-DM (30 m×0.25 mm) column. High performance liquid chromatography (HPLC) was performed on Hewlett-Packard 1100 Series chromatographs using Chiralpak AD column (0.46×25 cm) and AD guard (0.46×5 cm), Chiralcel OD-H (0.46×25 cm) and OD guard 0.46×5 cm) or Chiralpak AS (1.6×25 cm) and AS guard (1.6×5 cm) as noted. Optical rotations were taken using a Jasco P-1010 polarimeter (WI lamp, 589 nm, 25° C.).

The α,β-unsaturated ketones were prepared as described in the literature, as were the dienes: 3-penten-2-one, according to Chiu et al. (1998) *Synth. Commun.* 28:4513-4516; 4-octen-3-one, according to Chamberlin (1978) *Synth. Commun.* 8:579-581; 6-methylhept-4-en-3-one, according to Piers et al. (1975) *Can. R Chem.* 53:1281-1289; 2-methylhex-4-en-3-one, according to Bienvenue (1973) *J. Am. Chem. Soc.* 95:7345-7353; 6-methylhept-2-en-4-one, according to Bienvenue et al. (1969) *Bull. Soc. Chim. Fr.* pp. 391-396; buta-1,3-dienyl-carbamic acid benzyl ester, according to Jessup et al. (1980) *Org. Synth.* 59:1-9; 1-(methyleneallyl)-benzene, according to Marvel (1958) *J. Org. Chem.* 23:1658; and (5S)-5-benzyl-3-methyl-imidazolidin-4-one, according to Naef et al. (1985) *Helv. Chim. Acta* 85:135-143.

Known catalysts 1 and 2 ((5S)-5-benzyl-2,2,3-trimethylimidazolidin-4-one and (2S,5S)-5-benzyl-2-tert-butyl-3-methylimidazolidin-4-one, respectively) were prepared as described in the literature. See, e.g., U.S. Pat. No. 6,369,243 to MacMillan et al., U.S. Pat. No. 6,307,057 to MacMillan et al., Ahrendt et al. (2000), supra; Northrup et al. (2002) *J. Am. Chem. Soc.* 124(24):6798-6799, and U.S. patent application Ser. No. 10/187,635, filed Jul. 1, 2002.

EXAMPLE 1

(2R, 5R)-3-Methyl-2,5-diphenyl-imidazolidin-4-one (Catalyst 3): A solution of (R)-phenylglycine methyl amide (2.0 g, 12.2 mmol), benzaldehyde (990 μL, 9.7 mmol), and p-toluenesulfonic acid monohydrate (232 mg, 1.2 mmol) dissolved in 20 mL of methanol was heated to reflux for 16 hours. Concentration of the reaction mixture followed by silica gel chromatography (30-40% ethyl acetate in hexanes, linear gradient) afforded the title compound in 31% yield (750 mg, 3.0 mmol) and the more quickly eluting (2S, 5R)

isomer in 58% yield (1.43 g, 5.7 mmol). IR (film) 3478, 3324, 3086, 3063, 3031, 2958, 2917, 2863, 1959, 1890, 1814, 1698, 1603, 1477, 1456, 1428, 1400, 1343, 1281, 1204, 1107, 1069, 1027, 985.9, 935.2, 916.7, 868.6, 834.7, 732.9, 698.1 cm$^{-1}$; $^1$H NMR (300 MHz, CDCl$_3$) δ 7.41 (m, 10H, ArH), 5.33 (s, 1H, NCHN), 4.66 (s, 1H, CHCO), 2.65 (s, 3H, CH$_3$), 2.46 (s, 1H, NH); $^{13}$C NMR (75 MHz, CDCl$_3$) δ 173.4, 139.0, 138.6, 129.8, 129.3, 128.9, 128.3, 128.0, 127.7, 77.3, 63.7, 28.0; HRMS (CI) exact mass calc'd for (C$_{16}$H$_{16}$N$_2$O) requires m/z 252.1263, found m/z 252.1265. [α]$_D$=−8.6 (c=1.0, CHCl$_3$). The relative stereochemistry of catalyst 3 was confirmed by NOE studies.

EXAMPLE 2

(2S, 5S)-5-Benzyl-3-methyl-2-phenyl-imidazolidin-4-one (Catalyst 4): A solution of (S)-phenylalanine methyl amide (5.0 g, 28.1 mmol), benzaldehyde (3.14 mL, 30.9 mmol), and p-toluenesulfonic acid monohydrate (535 mg, 2.8 mmol) dissolved in 40 mL of methanol was heated to 50° C. for 24 hours. Concentration of the reaction mixture followed by silica gel chromatography (3:1 ethyl acetate:hexanes) afforded the title compound in 32% yield (2.38 g, 8.9 mmol) and the more quickly eluting (2R, 5S) isomer in 58% yield (4.32 g, 16.2 mmol). IR (film) 3479, 3331, 3085, 3061, 3030, 2921, 2861, 2242, 1959, 1891, 1815, 1696, 1603, 1494, 1475, 1436, 1370, 1335, 1282, 1206, 1098, 1028, 1002, 920.0, 760.0, 743.2, 700.7 cm$^{-1}$; $^1$H NMR (300 MHz, CDCl$_3$) δ 7.25 (m, 8H, ArH), 6.82 (m, 2H, ArH), 5.10 (m, 1H, NCHN), 3.84 (dd, J=4.5, 4.5 Hz, 1H, CHCO), 3.22 (dd, J=14.1, 5.7 Hz, 1H, one of CH$_2$Ph), 3.11 (dd, J=14.1, 4.5 Hz, 1H, one of CH$_2$Ph), 2.52 (s, 3H, CH$_3$), 1.87 (br s, 1H, NH); $^{13}$C NMR (75 MHz, CDCl$_3$) δ 174.6, 138.8, 137.1, 130.1, 129.7, 129.2, 129.1, 127.4, 127.1, 60.7, 37.2, 27.5; HRMS (CI) exact mass calc'd for (C$_{17}$H$_{18}$N$_2$O) requires m/z 266.1419, found m/z 266.1421. [α]$_D$=−101.8 (c=1.0, CHCl$_3$). The enantiopurity of the catalyst was confirmed (>99% ee) by HPLC analysis (AD column, 10% isopropanol in hexanes, 1 mL/min, 254 nm); (2S, 5S) isomer t$_r$=17.1 min, (2R, 5R) isomer t$_r$=15.5 min.

EXAMPLE 3

(2S, 5S)-5-Benzyl-3-methyl-2-(5-methyl-furan-2-yl)-imidazolidin-4-one (Catalyst 5): In an inert atmosphere glovebox, samarium (III) trifluoromethanesulfonate (1.20 g, 2.0 mmol) was added to a flame-dried 250 mL 3-neck round bottom flask fitted with a glass stopper, a septum, and a vacuum hose adapter followed by powdered 4 Å molecular sieves (4.0 g). Following removal from the glove-box, the reaction was placed under nitrogen and (S)-phenylalanine methyl amide (8.91 g, 50 mmol) was added as a solution in 80 mL of tetrahydrofuran immediately followed by freshly distilled (77° C., 14 mmHg, Vigreaux collumn) clear, colorless 5-methylfurfural (3.98 mL, 40 mmol). After stirring for 29 hours at room temperature, the reaction mixture was filtered through a plug of silica with dichloromethane, concentrated and purified by silica gel chromatography (1:1 ethyl acetate: hexanes) to afford the title compound as a clear, colorless oil in 46% yield (4.93 g, 18.2 mmol) and the faster eluting (2R, 5S) isomer as a pale yellow oil in 38% yield (4.10 g, 15.2 mmol). IR (film) 3482, 3325, 2922, 2862, 1695, 1563, 1495, 1477, 1453, 1402, 1326, 1267, 1218, 1098, 1021, 1006, 956.8, 938.9, 791.1, 734.4, 701.5 cm$^{-1}$; $^1$H NMR (300 MHz, CDCl$_3$) δ 7.26 (m, 5H, PhH), 6.11 (m, 1H, CHCHCH$_3$), 5.89 (m, 1H, CHCHCH$_3$ ), 5.19 (s, 1H, NCHN), 3.79 (dd, J=7.2, 4.5 Hz, 1H, CHCONMe), 3.26 (dd, J=14.4, 4.5 Hz, 1H, one of CH$_2$Ph), 3.09 (dd, J=14.1, 7.5 Hz, 1H, one of CH$_2$Ph), 2.64 (s, 3H, NCH$_3$), 2.21 (s, 3H, ArCH$_3$), 2.10 (br s, 1H, NH); $^{13}$C NMR (75 MHz, CDCl$_3$) δ 173.9, 153.5, 148.5, 137.3, 129.6, 128.9, 127.0, 111.2, 106.6, 71.3, 60.5, 37.8, 27.4, 14.0; HRMS (CI) exact mass calc'd for (C$_{16}$H$_{18}$N$_2$O$_2$) requires m/z 270.1368, found m/z 270.1368. [α]$_D$=−156.5 (g=1.0, CHCl$_3$). The enantiopurity of the catalyst was confirmed (>99% ee) by HPLC analysis (AD column, 5% isopropanol in hexanes, 1 mL/min, 254 nm); (2S, 5S) isomer t$_r$=22.9 min, (2S, 5R) isomer t$_r$=25.7 min. The relative stereochemistry of catalyst 5 was confirmed by NOE studies.

It will be appreciated that the methods of Examples 1-3 can be readily adapted for the synthesis of analogous catalysts, i.e., other imidazolidinones encompassed by formulae (IIA) and (IIB), by using appropriately substituted reactants as starting materials.

EXAMPLE 4

Effect of Catalyst Structure on Diels-Alder Reactions:

SCHEME 1

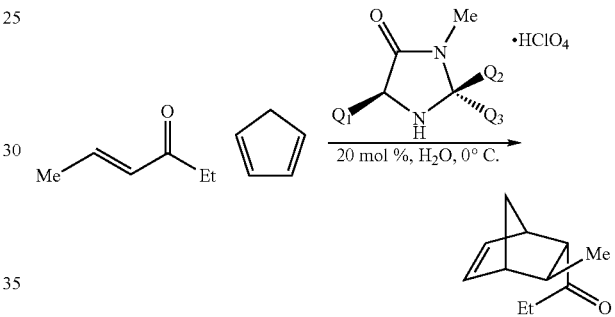

The Diels-Alder reaction of Scheme 1 was carried out to evaluate the effect of catalyst structure on enantioselectivity and reaction rate, using general procedure A, as follows.

General Procedure A: A 10-ml round-bottomed flask equipped with a magnetic stir bar and containing the catalyst (0.2 eq.) was either charged with H$_2$O (3-7M) or no solvent and cooled to 0° C. To the resulting suspension was added 4-hexen-3-one as the α, β-unsaturated ketone (1.0 eq.) followed by 70% aqueous perchloric acid (0.2 eq.). After stirring for 5 minutes, freshly distilled, pre-chilled cyclopentadiene (1.5 eq.) was added dropwise. The resulting biphasic mixture was stirred at constant temperature until complete consumption of the α,β-unsaturated ketone was observed as determined by TLC or GLC analysis. The reaction mixture was then diluted with the appropriate eluent, and then purified directly by silica gel chromatography.

The results obtained using known catalysts (1 and 2), and catalysts of the invention (3, 4, and 5) are set forth in Table 1:

TABLE 1

Effect of Amine Architecture on the Diels-Alder Reaction between 4-Hexen-3-one and Cyclopentadiene

| entry | catalyst | Q$_1$ | Q$_2$ (Q$_3$) | time (h) | % yield | endo:exo | % ee$^{a, b}$ |
|---|---|---|---|---|---|---|---|
| 1 | 1 | Bn | Me (Me) | 48 | 20$^c$ | 7:1 | 0 |
| 2 | 2 | Bn | t-Bu (H) | 48 | 27$^c$ | 9:1 | 0 |
| 3 | 3 | Ph | Ph (H) | 22 | 88 | 21:1 | 47 |

TABLE 1-continued

Effect of Amine Architecture on the Diels-Alder Reaction between 4-Hexen-3-one and Cyclopentadiene

| entry | catalyst | $Q_1$ | $Q_2$ ($Q_3$) | time (h) | % yield | endo:exo | % ee[a,b] |
|---|---|---|---|---|---|---|---|
| 4 | 4 | Bn | Ph (H) | 42 | 83 | 23:1 | 82 |
| 5 | 5 | Bn | 5-Me-furyl (H) | 22 | 89 | 25:1 | 90 |

[a]Product ratios determined by chiral GLC.
[b]Absolute configuration assigned by chemical correlation to a known compound.
[c]Less than 30% conversion of starting material after 48 h.

As may seen from the data in Table 1, known catalysts 1 and 2 were relatively ineffective with respect to both enantioselectivity and reaction rate (entries 1 and 2, 20-27% yield, 0% ee), despite their established utility with α,β-unsaturated aldehydes. See Ahrendt et al. (2000), Jen et al. (2000), and Paras et al. (2001), all cited supra. In contrast, the cis-2,5-1-substituted amine 3 provided useful reaction rates in conjunction with enantiocontrol (entry 3, 88% yield, 21:1 endo:exo, 47% ee). Efforts to increase enantioselectivity through iminium geometry control were successful with the introduction of a benzyl group at the C(2) catalyst site in catalyst 4 (entry 4, 83% yield, 82% ee). Moreover, substitution at C(5) with 2-(5-methylfuryl)-derived imidazolidinone in catalyst 5 afforded superior levels of enantiofacial discrimination while maintaining reaction efficiency (entry 5, 89% yield, 25:1 endo:exo, 90% ee).

Examples 5-11 were carried out to evaluate the effect of ketone structure on the Diels-Alder reaction of Example 4, according to Scheme 2:

SCHEME 2

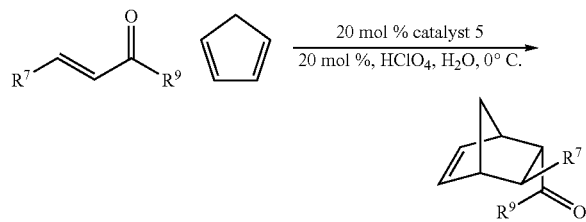

EXAMPLE 5

1-[(1R, 2R, 3S, 4R)-3-Methylbicyclo[2.2.1]hept-5-en-2-yl]-ethanone (Table 2, Entry 1): Prepared according to general procedure A from 3-penten-2-one (68 μL, 0.70 mmol), cyclopentadiene (69 μL, 0.84 mmol), 70% aqueous perchloric acid (12.1 μL, 0.14 mmol) and (2S, 5S)-5-benzyl-3-methyl-2-(5-methyl-furan-2-yl)-imidazolidin-4-one (37.8 mg, 0.14 mmol) in water (175 μL) for 2.5 hours at 0° C. Purification by silica gel chromatography (9:1 pentane:ether) provided the title compound as a colorless oil in 85% yield (89 mg, 0.59 mmol); 14:1 endo:exo, endo 61% ee. IR (film) 3061, 2962, 2871, 1708, 1461, 1426, 1359, 1333, 1267, 1183, 1170, 114, 1095, 1055, 906.8, 797.8, 719.4, 654.5, 597.0 cm$^{-1}$; $^1$H NMR (300 MHz, CDCl$_3$) δ 6.21 (dd, J=6.0, 3.3 Hz, 1 H, CH=CH), 5.90 (dd, J=5.7, 2.7 Hz, 1H, CH=CH), 3.13 (m, 1H, CHCH=CH), 2.44 (m, 1H, CHCH=CH), 2.42 (dd, J=4.8, 3.9 Hz, 1H, CHCO), 2.10 (s, 3H, CH$_3$CO), 1.86 (m, 1 H, CHCH$_3$), 1.57 (m, 1H, C(H)H), 1.43 (m, 1H, C(H)H), 1.14 (d, J=6.9 Hz, 3H, CHCH$_3$); $^{13}$C NMR (75 MHz, CDCl$_3$) δ 209.2, 138.8, 132.6, 61.9, 49.3, 46.6, 46.5, 35.9, 29.5, 21.4; HRMS (CI) exact mass calc'd for (C$_{10}$H$_{14}$O) requires nm/z 150.1045, found m/z 150.1041. [α]$_D$=+70.4 (c=1.0, CHCl$_3$). Product ratios were determined by GLC analysis (120° C., 23 psi); (1R, 2R, 3S, 4R) endo isomer t$_r$=6.9 min, and (1S, 2S, 3R, 4S) endo isomer t$_r$=6.3 min, exo isomers t$_r$=5.7, 5.5 min.

EXAMPLE 6

1-[(1R, 2R, 3S, 4R)-3-Methylbicyclo[2.2.1]hept-5-en-2-yl]-propan-1-one (Table 2, Entry 2): Prepared according to general procedure A from 4-hexen-3-one (70 μL, 0.61 mmol), cyclopentadiene (75 μL, 0.91 mmol), 70% aqueous perchloric acid (10.5 μL, 0.12 mmol) and (2S, 5S)-5-Benzyl-3-methyl-2-(5-methyl-furan-2-yl)-imidazolidin-4-one (30.7 mg, 0.12 mmol) in water (203 μL) for 22 hours at 0° C. Purification by silica gel chromatography (9:1 pentane:ether) provided the title compound as a colorless oil in 89% yield (88.7 mg, 0.54 mmol); 25:1 endo:exo, endo 90% ee. Product ratios were determined by GLC analysis (150° C., 23 psi); (1R, 2R, 3S, 4R) endo isomer t$_r$=3.7 min, and (1S, 2S, 3R, 4S) endo isomer t$_r$=3.6 min, exo isomers t$_r$=3.4, 3.5 min. H NMR, $^{13}$C NMR, and IR data 1 were consistent with previously reported values (Zhu et al. (1997) *J. Am. Chem. Soc.* 119:3507-3512; Ahrendt et al. (2000) *J. Am. Chem. Soc.* 122:4243-4244). [α]$_D$=+101.7 (c=1.0, CHCl$_3$).

Determination of the Absolute Stereochemistry of 1-[(1R, 2R, 3S, 4R)-3-methylbicyclo[2.2.1]hept-5-en-2-yl]-propan-1-one by Chemical Correlation to (1R, 2R, 3S, 4R)-3-methylbicyclo[2.2.1]hex-5-ene-2-carboxaldehyde (1R, 2R, 3S, 4R )-3-Methylbicyclo[2.2.1]hex-5-ene-2-carboxaldehyde (Ahrendt et al. (2000), supra) was treated with ethylmagnesium chloride followed by tetrapropylammonium perruthenate and 4-methylmorpholine N-oxide to afford 1-[(1R, 2R, 3S, 4R)-3-methylbicyclo[2.2.1]hept-5-en-2-yl]-propan-1-one; [α]$_D$=+105.5 (c=1.0, CHCl$_3$). The product was identical in all respects to the title compound.

EXAMPLE 7

1-[(1R, 2R, 3S, 4R)-3-Methylbicyclo[2.2.1]hept-5-en-2-yl]-pentan-1-one (Table 2, Entry 3): Prepared according to general procedure A from oct-2-en-4-one (89 μL, 0.60 mmol), cyclopentadiene (74 μL, 0.90 mmol), 70% aqueous perchloric acid (10.3 μL, 0.12 mmol) and (2S, 5S)-5-benzyl-3-methyl-2-(5-methyl-furan-2-yl)-imidazolidin-4-one (32.4 mg, 0.12 mmol) neat for 34 hours at 0° C. Purification by silica gel chromatography (19:1 hexanes:ethyl acetate) provided the title compound as a colorless oil in 83% yield (95.7 mg, 0.50 mmol); 22:1 endo:exo, endo 92% ee. IR (film) 3061, 2958, 2871, 1707, 1462, 1409, 1375, 1332, 1267, 1137, 1045, 904.4, 801.4, 715.9 cm$^{-1}$; $^1$H NMR (300 MHz, CDCl$_3$) δ 6.19 (dd, J=5.4, 3.0 Hz, 1H, CH=CH), 5.87 (dd, J=5.7, 2.7 Hz, 1H, CH=CH), 3.10 (br s, 1H, CHCH=CH), 2.43 (m, 1H, CHCH=CH), 2.39 (in, 3H, CHCO and CH$_2$CO), 1.86 (m, 1H, CHCH$_3$), 1.57-1.20 (m, 6H, COCH$_2$CH$_2$CH$_2$, and CHCH$_2$CH), 1.12 (d, J=6.9 Hz, 3H, CHCH$_3$), 0.87 (dd, J=7.5, 7.5 Hz, 3H, CH$_2$CH$_3$); $^{13}$C NMR (75 MHz, CDCl$_3$) δ 211.3, 138.6, 132.6, 61.2, 49.3, 46.6, 41.7, 35.9, 26.2, 22.8, 21.4, 14.3; HRMS (CI) exact mass calc'd for (C$_{13}$H$_{20}$O) requires m/z 192.1514, found m/z 192.1509. [α]$_D$=+89.3 (c=1.0, CHCl$_3$). Product ratios were determined by GLC analysis (150° C., 23 psi); (1R, 2R, 3S, 4R) endo isomer t$_r$=6.1 min, and (1S, 2S, 3R, 4S) endo isomer t$_r$=5.9 min, exo isomers t$_r$=5.5, 5.6 min.

Determination of the Absolute Stereochemistry of 1-[(1R, 2R, 3S, 4R)-3-methylbicyclol[2.2.1]hept-5-en-2-yl]-pentan-1-one by Correlation from (1R, 2R, 3S, 4R)-3-methylbicyclo[2.2.1]hex-5-ene-2-carboxaldehyde (1R, 2R, 3S, 4R)-3-Methylbicyclo-[2.2.1]hex-5-ene-2-carboxaldehyde was treated with n-butyllithium followed by tetrapropylammonium perruthenate and 4-methylmorpholine N-oxide to afford 1-[(1R, 2R, 3S, 4R)-3-methylbicyclo[2.2.1]hept-5-en-2-yl]-pentan-1-one; $[\alpha]_D$=+87.4 (c=1.0, CHCl$_3$). The product was identical in all respects to the title compound.

EXAMPLE 8

4-Methyl-1-[(1R, 2R, 3S, 4R)-3-methylbicyclo[2.2.1]hept-5-en-2-yl]-pentan-1-one (Table 2, Entry 4): Prepared according to general procedure A from 7-methyloct-2-en-4-one (82 µL, 0.50 mmol), cyclopentadiene (62 µL, 0.75 mmol), 70% aqueous perchloric acid (8.6 µL, 0.10 mmol) and (2S, 5S)-5-benzyl-3-methyl-2-(5-methyl-furan-2-yl)-imidazolidin-4-one (27 mg, 0.10 mmol) in water (167 µL) for 38 hours at 0° C. Purification by silica gel chromatography (19:1 hexanes:ethyl acetate) provided the title compound as a colorless oil in 86% yield (89 mg, 0.43 mmol); 20:1 endo:exo, endo 92% ee. IR (film) 3061, 2957, 2870, 1708, 1462, 1367, 1332, 1269, 1141, 1107, 1064, 904.7, 799.8, 716.2 cm$^{-1}$; $^1$H NMR (300 MHz, CDCl$_3$) δ 6.20 (dd, J=5.7, 3.0 Hz, 1H, CH=CH), 5.87 (dd, J=5.7, 2.7 Hz, 1H, CH=CH), 3.11 (m, 1H, CHCH=CH), 2.43 (m, 1H, CHCH=CH), 2.39 (m, 3H, CHCO and CH$_2$CO), 1.86 (m, 1H, CHCH$_3$), 1.58-1.37 (m, 5H, COCH$_2$CH$_2$CH, CHCH$_2$CH), 1.13 (d, J=6.9 Hz, 3H, CH$_2$CH$_3$), 0.86 (d, J=6.3 Hz, 6H, CH(CH$_3$)$_2$); $^{13}$C NMR (75 MHz, CDCl$_3$) δ 211.5, 138.6, 132.6, 61.2, 49.3, 46.6, 40.0, 35.9, 32.9, 28.1, 22.8, 22.7, 21.4; HRMS (CI) exact mass calc'd for (C$_{14}$H$_{22}$O) requires m/z 206.1671, found m/z 206.1671. $[\alpha]_D$=+89.4 (c=1.0, CHCl$_3$). Product ratios were determined by GLC analysis (150° C., 23 psi); (1R, 2R, 3S, 4R) endo isomer t$_r$=7.4 min, and (1S, 2S, 3R, 4S) endo isomer t$_r$=7.1 min, exo isomers t$_r$=6.6, 6.8 min.

Determination of the Absolute Stereochemistry of 4-methyl-1-[(1R, 2R, 3S, 4R)-3-methylbicyclo[2.2.1]hept-5-en-2-yl]-pentan-1-one by correlation with (1R, 2R, 3S, 4R)-3-methylbicyclo[2.2.1]hex-5-ene-2-carboxaldehyde (1R, 2R, 3S, 4R)-3-Methylbicyclo-[2.2.1]hex-5-ene-2-carboxaldehyde was treated with (3-methyl-butyl)-magnesium bromide followed by tetrapropylammonium perruthenate and 4-methylmorpholine N— oxide to afford 4-methyl-1-[(1R, 2R, 3S, 4R)-3-methylbicyclo[2.2.1]hept-5-en-2-yl]-pentan-1-one; $[\alpha]_{D=+81.2}$ (c=1.0, CHCl$_3$). The product was identical in all respects to the title compound.

EXAMPLE 9

2-Methyl-1-[3-methylbicyclo[2.2.1]hept-5-en-2-yl]-propan-1-one (Table 2, Entry 5) Prepared according to general procedure A from 2-methylhex-4-en-3-one (66 µL, 0.50 mmol), cyclopentadiene (62 µL, 0.75 mmol), 70% aqueous perchloric acid (8.6 µL, 0.10 mmol) and (2S, 5S)-5-benzyl-3-methyl-2-(5-methyl-furan-2-yl)-imidazolidin-4-one (27 mg, 0.10 mmol) in water (125 µL) for 48 hours at 0° C. Purification by silica gel chromatography (9:1 pentane:ether) provided the title compound as a colorless oil in 24% yield (22 mg, 0.12 mmol) as well as 29 mg recovered 2-methylhex-4-en-3-one; 8:1 endo:exo, endo 0% ee. IR (film) 3062, 2965, 2872, 1707, 1573, 1464, 1381, 1364, 1333, 1264, 1224, 1177, 1129, 1102, 1043, 1009, 908.1, 801.7, 724.5. 694.3 cm$^{-1}$; $^1$H NMR (300 MHz, CDCl$_3$) δ 6.23 (dd, J=6.0,3.3 Hz, 1H, CH=CH), 5.84 (dd, J=6.0, 2.7 Hz, 1H, CH=CH), 3.10 (m, 1H, CHCH=CH), 2.73 (dq, 1H, CH(CH$_3$)$_2$), 2.61 (dd, J=4.5, 3.3, 1H, CHCO), 2.46 (m, 1H, CHCH=CH), 1.87 (ddq, J=6.6, 1.8, 1.8 Hz, 1H, CHCHCO), 1.59 (m, 1H, one of CH$_2$), 1.44 (m, 1H, one of CH$_2$), 1.13 (d, J=7.2 Hz, 3H, CH$_3$CHCHCO), 1.07 (d, J=7.2 Hz, 3H, one of (CH$_3$)$_2$CH), 1.03 (d, J=6.9 Hz, 3H, one of (CH$_3$)$_2$CH); $^{13}$C NMR (75 MHz, CDCl$_3$) δ 215.3, 138.6, 132.5, 59.2, 49.4, 46.9, 46.8, 39.7, 35.9, 21.3, 19.4, 18.7; HRMS (CI) exact mass calc'd for (C$_{12}$H$_{18}$O) requires m/z 178.1358, found m/z 178.1356. $[\alpha]_D$=0.0 (c=1.0, CHCl$_3$). Product ratios were determined by GLC analysis (150° C., 23 psi); endo isomers t$_r$=3.8 min, 3.7 min, exo isomers t$_r$=3.6, 3.5 min.

EXAMPLE 10

1-[(1R, 2R, 3S, 4R)-3-Propylbicyclo[2.2.1]hept-5-en-2-yl]-propan-1-one (Table 2, Entry 6): Prepared according to general procedure A from oct-4-en-3-one (112 µL, 0.75 mmol), cyclopentadiene (93 µL, 1.13 mmol), 70% aqueous perchloric acid (12.9 µL, 0.15 mmol) and (2S, 5S)-5-benzyl-3-methyl-2-(5-methyl-furan-2-yl)-imidazolidin-4-one (40.5 mg, 0.15 mmol) in water (150 µL) for 32 hours at 0° C. Purification by silica gel chromatography (15:1 pentane:ether) provided the title compound as a colorless oil in 84% yield (120 mg, 0.62 mmol); 15:1 endo:exo, endo 92% ee. IR (film) 3060, 2961, 2872, 1710, 1459, 1413, 1377, 1333, 1216, 1106, 1017, 935.7, 904.3, 716.7 cm$^{-1}$; $^1$H NMR (300 MHz, CDCl$_3$) δ 6.22 (dd, J=6.0, 3.3 Hz, 1H, CH=CH), 5.84 (dd, J=5.4, 2.7 Hz, 1H, CH=CH), 3.12 (m, 1H, CHCH=CH), 2.57 (m, 1H, CHCH=CH), 2.45 (m, 3H, CH$_2$CO and CHCO), 1.83 (m, 1H, CH(nPr)), 1.59-1.19 (br m, 6H, CH$_3$CH$_2$CH$_2$, and CHCH$_2$CH), 1.02 (dd, J=6.0, 6.0 Hz, 3H, CH$_3$), 0.89 (dd, J=7.2, 7.2 Hz, 3H, CH$_3$); $^{13}$C NMR (75 MHz, CDCl$_3$) δ 211.7, 138.8, 132.4, 59.5, 47.3, 47.2, 46.6, 41.4, 38.7, 35.1, 22.3, 14.7, 8.3; HRMS (CI) exact mass calc'd for (CH$_{13}$H$_{20}$O) requires m/z 192.1514, found m/z 192.1512. $[\alpha]_D$=+91.5 (c=1.0, CHCl$_3$). Product ratios were determined by GLC analysis (150° C., 23 psi); (1R, 2R, 3S, 4R) endo isomer t$_r$=6.0 min, and (1S, 2S, 3R, 4S) endo isomer t$_r$=5.6 min, exo isomers t$_r$=5.1, 5.4 min.

EXAMPLE 11

1-[(1R, 2R, 3S, 4R)-3-Isopropylbicyclo[2.2.1]hept-5-en-2-yl]-propan-1-one (Table 2, Entry 7)

Prepared according to general procedure A from 6-methylhept-4-en-3-one (89 µL, 0.60 mmol), cyclopentadiene (99 µL, 1.2 mmol), 70% aqueous perchloric acid (10.3 µL, 0.12 mmol) and (2S, 5S)-5-benzyl-3-methyl-2-(5-methyl-furan-2-yl)-imidazolidin-4-one (32 mg, 0.12 mmol) in water (120 µL) for 2.5 days at 0° C. Then, an additional 1.2 mmol of cyclopentadiene was added and the mixture was allowed to stir for an additional 3.5 days at 0° C. Purification by silica gel chromatography (18:1 pentane:ether) provided the title compound as a colorless oil in 78% yield (90 mg, 0.47 mmol); 6:1 endo:exo, endo 90% ee. For the purpose of characterization, the more quickly eluting exo diastereomer was removed by silica gel chromatography as above. IR (film) 3057, 2961, 2869, 1709, 1460, 1367, 1334, 1136, 1028, 904.2, 716.6 cm–1; 1H NMR (300 MHz, CDCl$_3$) δ 6.26 (dd, J=5.7, 3.3 Hz, 1H, CH=CH), 5.79 (dd, J=5.7, 2.7 Hz, 1H, CH=CH), 3.14

(m, 1H, CHCH=CH), 2.77 (m, 1H, CHCH=CH), 2.63 (dd, J=3.6, 3.6 Hz, 1H, CHCO), 2.49 (m, 2H, CH$_2$CO), 1.40 (m, 3H, CH(CH$_3$)$_2$ and CHCH$_2$CH), 1.05 (d, J=7.5 Hz, 3H, one of CH(CH$_3$)$_2$), 0.99 (dd, J=4.8, 4.8 Hz, 3H, CH$_2$CH$_3$), 0.84 (d, J=7.5 Hz, 3H, one of CH(CH$_3$)$_2$), $^{13}$C NMR (75 MHz, CDCl$_3$) δ 211.6, 139.6, 131.9, 57.8, 49.1, 47.4, 47.2, 45.5, 35.2, 33.1, 22.7, 22.2, 8.5; HRMS (CI) exact mass calc'd for (C$_{13}$H$_{20}$O) requires m/z 192.1514, found m/z 192.1513. [α]$_D$=20.1 (c=1.0, CHCl$_3$). Product ratios were determined by GLC analysis (162° C., 23 psi); (1R, 2R, 3S, 4R) endo isomer t$_r$=4.4 min, and (1S, 2S, 3R, 4S) endo isomer t$_r$=4.2 min, exo isomers t$_r$=3.9, 4.1 min.

Table 2 summarizes the % yield, endo:exo ratio, and % ee for the reactions of Examples 5-11:

TABLE 2

Organocatalyzed Diels-Alder Cycloadditions between Cyclopentadiene and Representative Acyclic Enones

| entry | R$^7$ | R$^9$ | % yield | endo:exo | % ee$^{a,b}$ |
|---|---|---|---|---|---|
| 1 | Me | Me | 85 | 14:1 | 61 |
| 2 | Me | Et | 89 | 25:1 | 90 |
| 3 | Me | n-Bu | 83 | 22:1 | 92$^c$ |
| 4 | Me | i-Am | 86 | 20:1 | 92 |
| 5 | Me | i-Pr | 24 | 8:1 | 0 |
| 6 | n-Pr | Et | 84 | 15:1 | 92 |
| 7 | i-Pr | Et | 78 | 6:1 | 90 |

$^a$Product ratios determined by chiral GLC.
$^b$Absolute configuration determined by chemical correlation to a known compound or by analogy.
$^c$Reaction performed without solvent.

As may be deduced from Table 2, variation in the alkyl ketone group (R$^9$) reveals that ethyl, n-butyl, and isoamyl substituents (entries 2-4) provide for superior enantiocontrol (90-92% ee), while the methyl ketone is subject to moderate levels of induction (entry 1, 61% ee). The isopropyl-substituted ketone lead to racemic cycloadducts in relatively poor yield (entry 5, 0% ee, 24% contrast, variation in the steric contribution of the olefin substituent (R$^7$) did not result in loss of enantiocontrol or reaction efficiency (entries 2, 6, and 7, R$^7$=methyl, n-propyl, isopropyl, ≦78% yield, 6-25 to 1 endo: exo, 90-92% ee).

The following general procedure B was used to carry out Diels-Alder reactions between vinyl and ethyl ketone and various dienes, as described in Examples 12-16, according to Scheme 3.

SCHEME 3

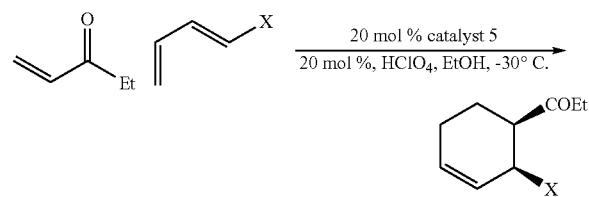

General procedure B: (2S, 5S)-5-Benzyl-3-methyl-2-(5-methylfuran-2-yl)-imidazolidin-4-one (5) was taken up in absolute ethanol (1-2M) and cooled to the appropriate temperature (−20 to −40° C.) with stirring. Ethyl vinyl ketone (1.0 eq.) was added to that chilled solution, followed by dropwise addition of 70% aqueous perchloric acid down the side of the flask. After stirring for 5 minutes, the diene (1.25-1.5 eq.) was added and the resulting solution was stirred at constant temperature until complete consumption of the α,β-unsaturated ketone was observed as determined by TLC or GLC analysis. The reaction mixture was then diluted with the appropriate eluent, and then purified directly by silica gel chromatography.

EXAMPLE 12

1-[(1R, 2S)-2-Methoxycyclohex-3-en-1-yl]-propan-1-one (Table 3, Entry 1): Prepared according to general procedure B from ethyl vinyl ketone (59 μL, 0.59 mmol), 1-methoxybutadiene (75 μL, 0.74 mmol) added via syringe pump over 12 hours, 70% aqueous perchloric acid (10.2 μL, 0.12 mmol) and (2S, 5S)-5-benzyl-3-methyl-2-(5-methyl-furan-2-yl)-imidazolidin-4-one (32 mg, 0.12 mmol) in ethanol (590 μL) for 3.5 days at −30° C. Purification by silica gel chromatography (9:1 pentane:ether) provided the title compound as a single diastereomer (as judged by GLC analysis) in 88% yield (88 mg, 0.52 mmol) and 92% ee. IR (film) 3027, 2975, 2937, 2879, 2821, 1715, 1452, 1432, 1375, 1211, 1191, 1129, 1108, 1084, 917.8, 889.2 cm$^{-1}$; $^1$H NMR (300 MHz, CDCl$_3$) δ 5.95 (m, 2H, CH=CH), 4.06 (m, 1H, CHOCH$_3$), 3.30 (s, 1H, OCH$_3$), 2.53 (m, 3H, CH$_2$CO and CHCO), 2.20 (m, 1H, one of CH$_2$CH=CH), 1.85 (m, 3H, CH$_2$CHCOEt and one of C(H)HCH=CH), 1.05 (dd, J=7.2, 7.2 Hz, 3H, CH$_2$CH$_3$); $^{13}$C NMR (75 MHz, CDCl$_3$) δ 211.5, 133.2, 124.5, 73.0, 56.7, 51.8, 33.8, 25.6, 18.7, 8.1; HRMS (CI) exact mass calc'd for [M—CH$_3$OH]+(C$_9$H$_{12}$O) requires m/z 136.0888, found m/z 136.0889. [α]$_D$=+16.7 (c=1.0, CHCl$_3$). Product ratios were determined by GLC analysis (100° C., 23 psi); (1R, 2S) endo isomer t$_r$=29.6 min, and (1S, 2R) endo isomer t$_r$=32.6 min, exo isomers t$_r$=19.1, 19.4 min.

EXAMPLE 13

Benzyl (1S, 6R)-6-propionylcyclohex-2-en-1-ylcarbamate (Table 3, Entry 2):

Concentrated (70% aqueous) perchloric acid (431 μL, 5.0 mmol) was added slowly to a stirring solution of ethyl vinyl ketone (2.49 mL, 25.0 mmol) and (2S, 5S)-5-benzyl-3-methyl-2-(5-methyl-furan-2-yl)-imidazolidin-4-one (1.35 g, 5.0 mmol) pre-chilled to −30° C. Then, buta-1,3-dienyl-carbamic acid benzyl ester (4.47g, 31.3 mmol) was added dropwise over 15 minutes as a solution in 12.5 mL of absolute ethanol. After stirring for 3.5 days, the reaction was diluted with ether (150 mL), washed successively with 1N HCl (50 mL), water (50 mL) and brine (25 mL). The organic layer was then dried over anhydrous magnesium sulfate, filtered and concentrated in vacuo to afford a pale brown oil. Purification by silica gel (8:1 hexanes:ethyl acetate) afforded the title compound as a single diastereomer (as judged by HPLC analysis) in 91% yield (5.17g, 22.7 mmol) and 98% ee. The combined aqueous extracts were treated with solid K$_2$CO$_3$, extracted with 3×50 mL portions of CHCl$_3$, dried over anhydrous Na$_2$SO$_4$ and concentrated in vacuo to afford a 91% recovery of (2S, 5S)-5-benzyl-3-methyl-2-(5-methyl-furan-2-yl)-imidazolidin-4-one (1.23 g, 4.55 mmol) after silica gel chromatography. IR (film) 3411, 3329, 3064, 3031, 2974, 2938, 2879, 2836, 1956, 1872, 1711, 1523, 1455, 1409, 1376, 1331, 1278, 1236, 1164, 1120, 1060, 1028, 988.9, 973.1, 775.6, 736.0, 697.9 cm$^{-1}$; $^1$H NMR (300 MHz, CDCl$_3$) δ 7.33 (m, 5H, ArH), 5.82 (m, 1H, CH=CH), 5.70 (m, 1H, CH=CH), 5.04 (m, 3H, CH$_2$Ph and NH), 4.63 (m, 1H, CHNH), 2.86 (ddd, J=10.2, 3.9, 3.9 Hz, 1H, CHCO), 2.70 (dq, J=18.0, 7.2 Hz, 1H, one of CH$_2$CO), 2.43 (dq, J=17.7, 7.2 Hz, 1H, one of CH$_2$CO), 2.10-1.65 (m, 4H, CH$_2$CH$_2$), 1.00 (dd, J=6.9, 6.9 Hz, 3H, CH$_3$); $^{13}$C NMR (75 MHz, CDCl$_3$) δ 212.0, 155.9, 136.6, 130.1, 128.7, 128.2, 128.1, 126.9, 67.0, 50.4, 46.9, 34.8, 24.2, 20.7, 8.0; HRMS (CI) exact mass calc'd for ($C_{17}H_{21}NO_3$) requires m/z 287.1521, found m/z 287.1519. $[\alpha]_D$=+122.0 (c=1.0, $CHCl_3$). Product ratios were determined by HPLC analysis (OD-H column, 3% ethanol in hexanes, 1 mL/min, 254 nm); (1S, 6R) endo isomer $t_r$=12.5 min, and (1R, 6S) endo isomer $t_r$=11.3 min, exo isomers $t_r$=8.6, 9.2 min.

EXAMPLE 14

1-[(1R)-4-Phenymcyclobex-3-en-1-yl]-propan-1-one (Table 3, Entry 3): Prepared according to general procedure B from ethyl vinyl ketone (48 μL, 0.48 mmol), 1-(methylene-allyl)-bnzene (83 μL, 0.60 mmol), 70% aqueous perchloric acid (8.2 μL, 0.10 mmol), (2S, 5S)-5-benzyl-3-methyl-2-(5-methyl-furan-2-yl)-imidazolidin-4-one (26 mg, 0.10 mmol), and 14.4 mg of anhydrous calcium chloride (as dessicant) in ethanol (160 μL) for 4 days and 10 hours at −40° C. Purification by silica gel chromatography (9:1 pentane:ether) provided the title compound as a single regioisomer (as judged by GLC analysis) in 92% yield (94 mg, 0.44 mmol) and 90% ee. IR (film) 3030, 2975, 2935, 2838, 1975, 1879, 1809, 1709, 1598, 1495, 1444, 1410, 1376, 1343, 1213, 1126, 1061, 1020, 958.4, 918.1, 868.1, 806.5, 743.2, 694.8 cm$^{-1}$; $^1$H NMR (300 MHz, $CDCl_3$) δ 7.35 (m, 5H, ArH), 6.12 (m, 1H, C=CH), 2.54 (m, 7H, $CH_2CO$, CHCO, $CH_2CH$, and allylic $CH_2CH_2$), 2.12 (m, 1H, C(H)H), 1.73 (m, 1H, C(H)H), 1.08 (dd, J=7.2, 7.2 Hz, 3H, $CH_3$); $^{13}$C NMR (75 MHz, $CDCl_3$) δ 214.2, 141.9, 136.4, 128.5, 127.1, 125.2, 123.0, 46.4, 34.4, 28.2, 27.5, 25.7, 8.2; HRMS (CI) exact mass calc'd for ($C_{15}H_{18}O$) requires m/z 214.1358, found m/z 214.1356. $[\alpha]_D$=+67.2 (c1.0, $CHCl_3$). Product ratios were determined by GLC analysis (150° C., 23 psi); (R) isomer $t_r$=62.4 min, and (S) isomer $t_r$=60.8 min, regioisomers $t_r$=49.6, 50.2 min.

EXAMPLE 15

1-[(1R, 2S)-2,4-Dimethylcyclohex-3-en-1-yl]-propan-1-one (Table 3, Entry 4): Prepared according to general procedure B from ethyl vinyl ketone (59 μL, 0.59 mmol), trans-2-methyl-1,3-pentadiene (94 μL, 0.89 mmol), 70% aqueous perchloric acid (10.2 μL, 0.12 mmol) and (2S, 5S)-5-benzyl-3-methyl-2-(5-methyl-furan-2-yl)-imidazolidin-4-one (32 mg, 0.12 mmol) in ethanol (590 μL) for 4.5 days at −30° C. Purification by silica gel chromatography (9:1 pentane:ether) provided the title compound as a single diastereomer (as judged by GLC analysis) in 90% yield (90 mg, 0.54 mmol) and 90% ee. IR (film) 2964, 2937, 2874, 2833, 1711, 1452, 1377, 1343, 1227, 1195, 1123, 1038, 984.2, 886.0, 841.6 cm$^{-1}$; $^1$H NMR (300 MHz, $CDCl_3$) δ 5.37 (m, 1H, CH=$CCH_3$), 2.60 (m, 2H, CHCO and $CHCH_3$), 2.50 (dq, J=17.4, 7.5 Hz, 1H, C(H)HCO), 2.37 (dq, J=17.4, 7.5 Hz, 1H, C(H)HCO), 1.94 (m, 2H, =$CCH_2$), 1.68 (m, 2H, $CH_2CH$), 1.64 (s, 3H, $CH_3C$=CH), 1.05 (dd, J=7.5, 7.5 Hz, 3H, $CH_2CH_3$), 0.76 (dd, J=6.9, 6.9 Hz, 3H, $CH_3CH$); $^{13}$C NMR (75 MHz, $CDCl_3$) δ 214.0, 133.7, 126.3, 50.5, 34.6, 31.7, 30.2, 23.8, 19.0, 16.8, 8.1. $[\alpha]_D$=+16.7 (c=1.0, $CHCl_3$). Product ratios were determined by GLC analysis (100° C., 23 psi); (1R, 2S) endo isomer $t_r$=21.3 min, and (1S, 2R) endo isomer $t_r$=20.4 min, exo isomers $t_r$=15.4, 16.6 min.

EXAMPLE 16

1-[(1R)-4-Methylcyclohex-3-en-1-yl]-propan-1-one (Table 3, Entry 5): Prepared according to general procedure B from ethyl vinyl ketone (70 μL, 0.70 mmol), isoprene (140 μL, 1.40 mmol), 70% aqueous perchloric acid (12.1 μL, 0.14 mmol) and (2S, 5S)-5-benzyl-3-methyl-2-(5-methyl-furan-2-yl)-imidazolidin-4-one (38 mg, 0.14 mmol) neat for 3 days at −20° C. Then, another portion of isoprene (100 μL, 1.00 mmol) was added and the solution was allowed to stir for an additional 3 days. Purification by silica gel chromatography (10:1 pentane:ether) provided the title compound as a single regioisomer (as judged by GLC analysis) in 79% yield (84 mg, 0.55 mmol) and 85% ee. IR (film) 2967, 2928, 2836, 1710, 1452, 1413, 1377, 1343, 1217, 1149, 1126, 952.6, 915.1, 871.9, 800.0 cm$^{-1}$; $^1$H NMR (300 MHz, $CDCl_3$) δ 5.34 (m, 1H, C=CH), 2.46 (m, 3H, $CH_2CO$ and CHCO), 2.09 (m, 2H, $CH_2CH$=C($CH_3$)), 1.94 (m, 2H, $CH_2C(CH_3)$=CH), 1.86 (m, 1H, one of $CH_2CH_2CH$), 1.54 (m, 1H, one of $CH_2CH_2CH$), 0.99 (dd, J=7.5, 7.5 Hz, 3H, $CH_2CH_3$); $^{13}$C NMR (75 MHz, $CDCl_3$) δ 214.4, 133.8, 119.6, 46.6, 34.1, 29.9, 27.6, 25.4, 23.7, 8.1; HRMS (CI) exact mass calc'd for ($C_{10}H_{16}O$) requires m/z 152.1201, found m/z 152.1201. $[\alpha]_D$=+37.8 (c=1.0, $CHCl_3$). Product ratios were determined by GLC analysis (100° C., 23 psi); (R) isomer $t_r$=16.1 min, and (S) isomer $t_r$=15.4 min.

Determination of the Absolute Stereochemistry of 1-[(1R)-4-methylcyclohex-3-en-1-yl]-propan-1-one by Correlation from (1R)-4-methyl-3-cyclohexene-1 Carboxaldehyde (1R)-4-Methyl-3-cyclohexene-1-carboxaldehyde was treated with ethylmagnesium bromide followed by tetrapropylammonium perruthenate and 4-methylmorpholine N-oxide to afford 1-[(1R)-4-methylcyclohex-3-en-1-yl]-propan-1-one; $[\alpha]_D$=+41.3 (c=1.0, $CHCl_3$). The product was identical in all respects to the title compound.

Table 3 summarizes the % yield, endo:exo ratio, and % ee for the reactions of Examples 12-16:

TABLE 3

Organocatalyzed Diels-Alder Cycloadditions between Ethyl Vinyl Ketone and Representative Dienes.

| entry | diene | product | endo:exo | % yield | % ee[a, b] |
|---|---|---|---|---|---|
| 1 | ⟋⟍OMe | COEt / OMe | >200:1 | 88 | 96 |
| 2 | ⟋⟍NHCbz | COEt / NHCbz | >100:1 | 91 | 98 |

TABLE 3-continued

Organocatalyzed Diels-Alder Cycloadditions between Ethyl Vinyl Ketone and Representative Dienes.

| entry | diene | product | endo:exo | % yield | % ee[a, b] |
|---|---|---|---|---|---|
| 3[c] | Ph-diene with Ph | cyclohexenyl-COEt with Ph | >200:1 | 92 | 90 |
| 4 | Me-diene-Me | cyclohexenyl-COEt with Me, Me | >200:1 | 90 | 90 |
| 5[e] | Me-diene | cyclohexenyl-COEt with Me | >200:1[d] | 79 | 85[f] |

[a] Product ratios determined by chiral GLC or HPLC.
[b] Absolute configuration determined by chemical correlation to a known compound or by analogy.
[c] Reaction conducted at −40° C.
[d] Regiomeric ratio.
[e] Reaction conducted at −20° C.
[f] Reaction performed without solvent.

As indicated in Table 3, the catalyst was quite general with respect to diene structure, allowing enantioselective access to a broad range of alkyl-, alkoxy-, amino-, and aryl-substituted cyclohexenyl ketones (Table 3, entries 1-5, 79-92% yield, >100 to 1 endo:exo, 85-98% ee). All reactions produced a single regio- and diastereomer as determined by GLC (>200:1) or HPLC (>100:1) analysis. The reaction of entry 2 (Example 13), i.e., the cycloaddition of dienylamine 6 to ethyl vinyl ketone, indicates both the functional group tolerance and the preparative utility of the catalyst.

Examples 17-21 set forth representative procedures for carrying out Diels-Alder cycloadditions between cyclopentadiene and cyclic enones, as illustrated in Scheme 4:

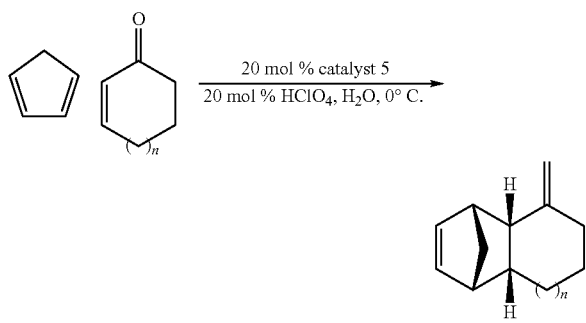

SCHEME 4

EXAMPLE 17

(1R, 2R, 6R, 7R)-Tricyclo[5.2.1.0~2,6~]dec-8-en-3-one (Table 4, Entry 1): Prepared according to general procedure A from 2-cyclopenten-1-one (50 μL, 0.60 mmol), cyclopentadiene (74 μL, 0.90 mmol), 70% aqueous perchloric acid (10.3 μL, 0.12 mmol) and (2S, 5S)-5-benzyl-3-methyl-2-(5-methyl-furan-2-yl)-imidazolidin-4-one (32.4 mg, 0.12 mmol) in water (150 μL) for 12 hours at 0° C. Purification by silica gel chromatography (5:1 pentane:ether) provided the title compound as a volatile white powder in 81% yield (72 mg, 0.49 mmol); 15:1 endo:exo, endo 48% ee. IR (film) 3058, 2964, 2941, 2868, 1730, 1475, 1402, 1341, 1318, 1225, 1172, 1129, 1090, 1040, 936.0, 902.3, 840.8, 804.2, 732.8 cm$^{-1}$; $^{1}$H NMR (300 MHz, CDCl$_3$) δ 6.22 (dd, J=5.7, 2.7 Hz, 1H, CH=CH), 6.11 (dd, J=5.7, 3.0 Hz, 1H, CH=CH), 3.19 (m, 1H, CHCH=CH), 3.00 (m, 1H, CHCH=CH), 2.97 (m, 1H, CHCO), 2.85 (m, 1H, C(H)HCO), 2.02 (m, 4H, CHCH$_2$CH$_2$, C(H)HCO, and CHCH$_2$CH), 1.48 (m, 2H, CH$_2$CH$_2$CO); $^{13}$C NMR (75 MHz, CDCl$_3$) δ 222.6, 136.3, 135.0, 54.7, 52.6, 47.8, 47.4, 41.6, 40.9, 23.1; HRMS (CI) exact mass calc'd for (C$_{10}$H$_{12}$O) requires m/z 148.0888, found m/z 148.0887. [α]$_D$+122.3 (c=1.0, CHCl$_3$). Product ratios were determined by GLC analysis (140° C., 23 psi); (1R, 2R, 6R, 7R) endo isomer t$_r$=7.1 min, and (1S, 2S, 6S, 7S) endo isomer t$_r$=6.7 min, exo isomers t$_r$=6.1 min.

EXAMPLE 18

(1R, 2R, 7R, 8R)-Tricyclo[6.2.1.0~2,7~]undec-9-en-3-one (Table 4, Entry 2): Prepared according to general procedure A from 2-cyclohexen-1-one (58 μL, 0.60 mmol), cyclopentadiene (74 μL, 0.90 mmol), 70% aqueous perchloric acid (10.3 μL, 0.12 mmol), and (2S, 5S)-5-benzyl-3-methyl-2-(5-methyl-furan-2-yl)-imidazolidin-4-one (32.4 mg, 0.15 mmol) in water (150 μL) for 17 hours at 0° C. Purification by silica gel chromatography (5:1 pentane:ether) provided the title compound as a colorless oil in 81% yield (79 mg, 0.49 mmol); 12:1 endo:exo, endo 63% ee. For the purposes of characterization, the endo isomer was separated from the exo isomer by silica gel chromatography. IR (film) 3061, 2961, 2935, 2867, 1701, 1570, 1453, 1406, 1358, 1337, 1315, 1236, 1172, 1115, 1018, 910.6, 823.8, 779.2, 733.6, 561.5 cm$^{-1}$; $^{1}$H NMR (300 MHz, CDCl$_3$) δ 6.15 (dd, J=5.7, 3.0 Hz, 1H, CH=CH), 5.99 (dd, J=5.7, 3.0 Hz, 1H, CH=CH), 3.24 (m, 1H, CHCH=CH), 2.85 (m, 1H, CHCH=CH), 2.66 (m, 2H, CH(H)CO and CHCO), 2.30 (m, 1H, one of CH$_2$CO), 1.79

(m, 4H, CHCHCH$_2$, COCH$_2$CH$_2$ and one of CHCHCH$_2$), 1.42 (ddd, J=8.4, 1.8, 1.8 Hz, 1H, one of CHCH$_2$CH), 1.28 (m, 1H, one of CHCH$_2$CH), 0.73 (m, 1H, one of CHCHCH$_2$); $^{13}$C NMR (75 MHz, CDCl$_3$) δ215.7, 137.8, 135.1, 52.0, 48.7, 46.8, 45.5, 41.7, 39.7, 28.4, 22.2; HRMS (CI) exact mass calc'd for (C$_{11}$H$_{14}$O) requires m/z 162.1045, found m/z 162.1049. [α]$_D$=+120.6 (c=1.0, CHCl$_3$). Product ratios were determined by GLC analysis (130° C., 23 psi); (1R, 2R, 7R, 8R) endo isomer t$_r$=13.4 min, and (1S, 2S, 7S, 8S) endo isomer t$_r$=13.2 min, exo isomers t$_r$=11.7, 12.3 min.

EXAMPLE 19

(1R, 2R, 8R, 9R)-Tricyclo[7.2.1.0~2,6~]dodec-10-en-3-one (Table 4, Entry 3): Prepared according to general procedure A from 2-cyclohepten-1-one (67 µL, 0.60 mmol), cyclopentadiene (74 µL, 1.13 mmol), 70% aqueous perchloric acid (10.2 µL, 0.12 mmol) and (2S, 5S)-5-benzyl-3-methyl-2-(5-methyl-furan-2-yl)-imidazolidin-4-one (32.4 mg, 0.12 mmol) in water (150 µL) for 28 hours at 0° C. Purification by silica gel chromatography (5:1 pentane:ether) provided the title compound as a colorless oil in 85% yield (90 mg, 0.51 mmol); 18:1 endo:exo,endo 90% ee. IR(film)2958, 2930, 2862, 1700, 1455, 1405, 1335, 1289, 1246, 1166, 1125, 1066, 949.6, 912.0, 860.4, 776.5, 722.9, 580.5, 554.0 cm$^{-1}$; $^1$H NMR (300 MHz, CDCl$_3$) δ 6.39 (dd, J=5.4, 2.7 Hz, 1H, CH=CH), 5.91 (dd, J=5.4, 3.0 Hz, 1H, CH=CH), 3.17 (dd, J=10.2, 3.3 Hz, 1H, CHCO), 2.99 (m, 1H, CHCH=CH), 2.70 (m, 1H, CHCH=CH), 2.44 (m, 2H, CH$_2$CO), 2.21 (m, 1H, CHCHCO), 1.96-1.28 (br m, 7H, CHCH$_2$CH, COCH$_2$CH$_2$CH$_2$, and one of CHCHCH$_2$), 0.74 (m, 1H, one of CHCHCH$_2$); $^{13}$C NMR (75 MHz, CDCl$_3$) δ 213.9, 137.7, 132.5, 58.6, 48.9, 48.1, 45.1, 43.0, 41.8, 30.8, 27.6, 23.2; HRMS (CI) exact mass calc'd for (C$_{12}$H$_{16}$O) requires m/z 176.1201, found m/z 176.1201. [α]$_D$=+9.1 (c=1.0, CHCl$_3$). Product ratios were determined by GLC analysis (140° C., 23 psi); (1R, 2R, 8R, 9R) endo isomer t$_r$=13.2 min, and (1S, 2S, 8S, 9S) endo isomer t$_r$=12.8 min, exo isomers t$_r$=11.8, 15.0 min.

EXAMPLE 20

(1R, 2R, 9R, 10R)-Tricyclo[8.2.1.0~2,6~]tridec-11-en-3-one (Table 4, Entry 4): Prepared according to general procedure A from 2-cycloocten-1-one (82 µL, 0.60 mmol), cyclopentadiene (74 µL, 1.13 mmol), 70% aqueous perchloric acid (10.2 µL, 0.12 mmol) and (2S, 5S)-5-benzyl-3-methyl-2-(5-methyl-furan-2-yl)-imidazolidin-4-one (32.4 mg, 0.12 mmol) in water (240 µL) for 72 hours at 0° C. Purification by silica gel chromatography (19:1 pentane:ether) provided the title compound as a colorless oil in 83% yield (95 mg, 0.50 mmol); 6:1 eindo:exo, endo 91% ee. IR (film) 3060, 2928, 2856, 1701, 1454, 1338, 1290, 1222, 1175, 1073, 1019, 895.9, 838.2, 716.9 cm$^{-1}$; $^1$H NMR (300 MHz, CDCl$_3$) δ 6.49 (dd, J=5.4, 2.7 Hz, 1H, CH=CH), 5.98 (dd, J=5.4, 2.7 Hz, 1H, CH=CH), 3.29 (dd, J=8.1, 3.3 Hz, 1H, CHCO), 2.90 (m, 1H, CHCH=CH), 2.72 (m, 1H, CHCH=CH), 2.49 (m, 2H, CH$_2$CO), 2.15 (m, 1H, CHCHCO), 1.82 (m, 2H, COCH$_2$CH$_2$), 1.63 (m, 1H, one of COCH$_2$CH$_2$C(H)H), 1.32 (m, 3H, COCH$_2$CH$_2$C(H)H, and CHCH$_2$CH$_2$), 1.08 (m, 1H, CHC(H)H), 0.78 (m, 1H, , CHC(H)H); $^{13}$C NMR (75 MHz, CDCl$_3$) δ 215.9, 137.9, 132.0, 56.0, 50.9, 49.5, 48.3, 48.0, 47.4, 31.3, 30.9, 28.5, 23.6. [α]$_D$=−69.9 (c=1.0, CHCl$_3$). Product ratios were determined by GLC analysis (150° C., 23 psi); (1R, 2R, 9R, 10R) endo isomer t$_r$=12.8 min, and (1S, 2S, 9S, 10S) endo isomer t$_r$=12.4 min, exo isomers t$_r$=11.2, 10.6 min.

EXAMPLE 21

(1R, 2R, 16S, 17R)-Tricyclo[15.2.1.0~2,16~]eicos-18-en-3-one (Table 4, Entry 5): Prepared according to general procedure A from trans-2-cyclopentadecen-1-one (100 mg, 0.45 mmol), cyclopentadiene (56 µL, 0.67 mmol), 70% aqueous perchloric acid (7.8 µL, 0.09 mmol) and (2S, 5S)-5-benzyl-3-methyl-2-(5-methyl-furan-2-yl)-imidazolidin-4-one (24.3 mg, 0.09 mmol) in water (150 µL) for 72 hours at 0° C. Purification by flash chromatography (9:1 ethyl acetate:hexanes) provided the title compound as a clear, colorless crystalline solid in 88% yield (114 mg, 0.50 mmol); 5:1 endo:exo, endo 93% ee. IR (film) 3052, 2922, 2854, 1698, 1456, 1368, 1331, 1225, 1126, 1084, 1016, 905.5, 884.9, 714.4 cm$^{-1}$; $^1$H NMR (300 MHz, CDCl$_3$) δ 6.21 (dd, J=5.4, 2.7 Hz, 1H, CH=CH), 5.86 (dd, J=5.4, 2.7 Hz, 1H, CH=CH), 3.09 (m, 1H, CHCH=CH), 2.61 (m, 2H, CHCO and one of CH$_2$CO), 2.52 (m, 1H, CHCH=CH), 2.41 (m, 1H, one of CH$_2$CO), 2.27 (m, 1H, CHCHCO), 1.81-1.24 (br m, 22H, (CH$_2$)$_{11}$); $^{13}$C NMR (75 MHz, CDCl$_3$) δ 211.6, 138.5, 132.6, 59.6, 48.4, 47.2, 46.7, 41.5, 41.3, 36.3, 28.0, 27.9, 27.7, 27.2, 26.8, 26.8, 26, 26.7 26.0, 23.6. [α]$_D$=+22.2 (c=1.0, CHCl$_3$). Product ratios were determined by GLC analysis (200° C., 23 psi); (1R, 2R, 16S, 17S) endo isomer t$_r$=20.1 min, and (1S, 2S, 16R, 17R) endo isomer t$_r$=19.6 min, exo isomers t$_r$=19.0, 18.6 min. The trans relative stereochemistry of C-16 and C-17 was confirmed by the presence of an NOE between the C-16 methine proton and the two C-19 protons.

Table 4 summarizes the reaction time, % yield, endo:exo ratio, and % ee for the reaction of Examples 17-21:

TABLE 4

Organocatalyzed Diels-Alder Cycloadditions between Cyclopentadiene and Representative Cyclic Enones

| entry | n | time (h) | % yield | endo:exo | % ee$^{a, b}$ |
|---|---|---|---|---|---|
| 1 | 0 | 12 | 81 | 15:1 | 48 |
| 2 | 1 | 17 | 81 | 12:1 | 63 |
| 3 | 2 | 28 | 85 | 18:1 | 90 |
| 4 | 3 | 72 | 83 | 6:1 | 91 |
| 5 | 10 | 72 | 88$^c$ | 5:1 | 93 |

$^a$Product ratios determined by chiral GLC.
$^b$Absolute configuration determined by chemical correlation to a known compound.
$^c$Reaction performed with (E)-cyclopentadecene-2-one to provide the corresponding 1,2-trans-tricyclo[15.2.1.0]eicos-18-en-3-one.

As may be seen in the table, cyclopentenone and cyclohexanone provided for modest enantiocontrol (12-15:1 endo:exo, 48-63% ee, 81% yield), while cycloheptenone (n=2), cyclooctenone (n=3), and (E) cyclopentadecene-2-one (n=10) were found to be highly enantioselective (entries 3-5, 5-18:1 endo:exo, 90-93% ee, 83-88% yield). Cyclopentenone (n=0, entry 1) and cyclohexanone (n=1, entry 2) were found to be somewhat less enantioselective.

We claim:

1. A compound composed of an acid addition salt of the structure of formula (IIA) or (IIB)

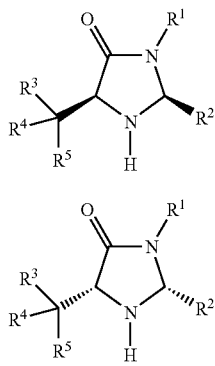

(IIA)

(IIB)

wherein:
R$^1$ is methyl;
R$^2$ is 5-methylfuryl;
R$^5$ is phenyl; and
R$^3$ and R$^4$ are hydrogen.

2. The compound of claim 1, wherein the compound is an acid addition salt of the structure of formula (IIA).

3. The compound of claim 1, wherein the compound is an acid addition salt of the structure of formula (IIB).

4. The compound of claim 1, wherein the acid addition salt is formed with a Bronsted acid.

5. The compound of claim 4, wherein the Bronsted acid is selected from the group consisting of acids having a pK$_a$ less than about 5 and combinations thereof.

6. The compound of claim 5, wherein the Bronsted acid is an inorganic acid.

7. The compound of claim 6, wherein the Bronsted acid is selected from the group consisting of hydrochloric acid, hydrobromic acid, sulfuric acid, sulfurous acid, nitric acid, nitrous acid, perchloric acid, phosphoric acid, chromic acid, and combinations thereof.

8. The compound of claim 5, wherein the Bronsted acid is an organic acid.

9. The compound of claim 8, wherein the organic acid is selected from the group consisting of carboxylic acids, sulfonic acids, phosphonic acids, and phenols substituted with 1 to 5 electron-withdrawing substituents.

10. The compound of claim 8, wherein the organic acid is selected from the group consisting of acetic acid, propionic acid, glycolic acid, pyruvic acid, oxalic acid, malic acid, malonic acid, succinic acid, maleic acid, fumaric acid, tartaric acid, citric acid, benzoic acid, 2-nitrobenzoic acid, cinnamic acid, mandelic acid, methanesulfonic acid, ethanesulfonic acid, triflic acid, p-toluenesulfonic acid, salicylic acid, chloroacetic acid, dichloroacetic acid, trichloroacetic acid, trifluoroacetic acid, and combinations thereof.

11. The compound of claim 1, wherein the compound is covalently bound, directly or indirectly, to a solid support.

12. A process for catalyzing a reaction between an α,β-unsaturated ketone and a second reactant by lowering the energy level of the lowest unoccupied molecular orbital (LUMO) of the ketone, comprising:
contacting an α,β-unsaturated ketone with the second reactant in the presence of an imidazolidinone catalyst and an acid, wherein the catalyst has the structure of formula (IIA) or (IIB)

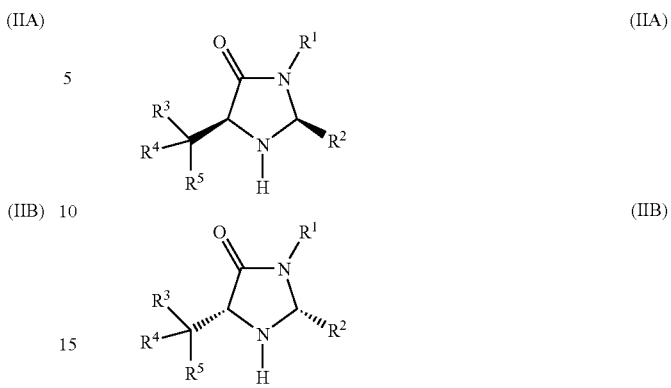

(IIA)

(IIB)

in which R$^1$ is methyl, R$^2$ is 5-methylfuryl, R$^5$ is phenyl, and R$^3$ and R$^4$ are hydrogen, and further wherein the second reactant is capable of reacting with the ketone by virtue of the lowered LUMO of the ketone in the presence of the catalyst, and further wherein the second reactant has the structure of formula (IV)

(IV)

wherein:
R$^{11}$ is selected from the group consisting of hydrogen, C$_1$-C$_{30}$ hydrocarbyl, substituted C$_1$-C$_{30}$ hydrocarbyl, heteroatom-containing C$_1$-C$_{30}$ hydrocarbyl, and substituted C$_1$-C$_{30}$ heteroatom-containing hydrocarbyl;

Q is a five- or six-membered aromatic ring containing zero to 3 heteroatoms selected from N, O and S and zero to 4 nonhydrogen substituents, wherein any two adjacent nonhydrogen substituents may together form an additional C$_5$-C$_{30}$ aryl, substituted C$_5$-C$_{30}$ aryl, C$_5$-C$_{30}$ heteroaryl, or substituted C$_5$-C$_{30}$ heteroaryl substituent; and X is N or CR$^{13}$ wherein R$^{13}$ is hydrogen, C$_1$-C$_{30}$ hydrocarbyl, substituted C$_1$-C$_{30}$ hydrocarbyl, heteroatom-containing C$_1$-C$_{30}$ hydrocarbyl, or substituted heteroatom-containing C$_1$-C$_{30}$ hydrocarbyl.

13. The process of claim 12, wherein the α,β-unsaturated ketone has the structure of formula (III)

(III)

in which R$^6$, R$^7$, and R$^8$ are independently selected from the group consisting of hydrogen, C$_1$-C$_{30}$ hydrocarbyl, heteroatom-containing C$_1$-C$_{30}$ hydrocarbyl, substituted C$_1$-C$_{30}$ hydrocarbyl, substituted heteroatom-containing C$_1$-C$_{30}$ hydrocarbyl, and functional groups, and R$^9$ is —CH$_2$—CH$_2$—R$_{10}$ where R$^{10}$ is hydrogen, C$_1$-C$_{12}$ hydrocarbyl, substituted $C_1$-$C_{12}$ hydrocarbyl, heteroatom-containing $C_1$-$C_{12}$ hydrocarbyl, or substituted $C_1$-$C_{12}$ hydrocarbyl.

14. The process of claim 13, wherein:
$R^6$, $R^7$, and $R^8$ are independently selected from the group consisting of hydrogen, $C_1$-$C_{24}$ alkyl, $C_2$-$C_{24}$ alkenyl, $C_2$-$C_{24}$ alkynyl, $C_2$-$C_{24}$ alkoxy, $C_2$-$C_{24}$ alkenyloxy, $C_2$-$C_{24}$ alkynyloxy, $C_5$-$C_{30}$ aryl, $C_5$-$C_{30}$ aryloxy, $C_2$-$C_{24}$ alkoxyalkyl, $C_6$-$C_{30}$ aryloxyalkyl, hydroxyl, sulfhydryl, $C_2$-$C_{24}$ alkylcarbonyl, $C_6$-$C_{30}$ arylcarbonyl, $C_2$-$C_{24}$ alkoxycarbonyl, $C_6$-$C_{30}$ aryloxycarbonyl, halocarbonyl, $C_2$-$C_{24}$ alkylcarbonato, $C_6$-$C_{30}$ arylcarbonato, carboxy, carboxylato, carbamoyl, mono- and di-($C_1$-$C_{24}$ alkyl)-substituted carbamoyl, mono- and di-($C_5$-$C_{20}$ aryl)-substituted carbamoyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{30}$ arylamido, imino, $C_2$-$C_{24}$ alkylimino, $C_6$-$C_{30}$ arylimino, nitro, nitroso, sulfo, sulfonato, $C_1$-$C_{24}$ alkylsulfanyl, $C_5$-$C_{30}$ arylsulfanyl, $C_1$-$C_{24}$ alkylsulfinyl, $C_5$-$C_{30}$ arylsulfinyl, $C_1$-$C_{24}$ alkylsulfonyl, $C_5$-$C_{30}$ arylsulfonyl, phosphono, phosphonato, phosphinato, phospho, phosphino, and combinations thereof, and further wherein any two of $R^6$, $R^7$, and $R^8$ taken together can form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and
$R^{10}$ is hydrogen, $C_1$-$C_6$ alkyl, or substituted $C_1$-$C_6$ alkyl
$R_{10}$ is hydrogen, $C_1$-$C_6$ alkyl, or substituted $C_1$-$C_6$ alkyl.

15. The process of claim 14, wherein $R^6$ and $R^8$ are hydrogen.

16. The process of claim 15, wherein $R^7$ is selected from the group consisting of hydrogen, $C_1$-$C_{12}$ alkyl, $C_1$-$C_{12}$ alkoxy, $C_5$-$C_{20}$ aryl, $C_2$-$C_{12}$ alkoxyalkyl, and $C_6$-$C_{20}$ aryloxyalkyl.

17. The process of claim 16, wherein $R^7$ is selected from the group consisting of hydrogen, $C_1$-$C_6$ alkyl, $C_5$-$C_{12}$ aryl, and $C_6$-$C_{12}$ aryloxyalkyl, and $R^{10}$ is hydrogen, methyl, ethyl, or n-propyl.

18. The process of claim 13, wherein the second reactant is directly or indirectly bound to the ketone, such that the reaction is intramolecular.

19. The process of claim 13, wherein the reaction is selected from the group consisting of cyclo addition reactions, 1,4 nucleophilic conjugate addition reactions, 1,4 radical addition reactions, organometallic insertions reactions, ene reactions, and any combination thereof occurring in tandem.

20. The process of claim 19, wherein the reaction is a cycloaddition reaction.

21. The process of claim 20, wherein the cycloaddition reaction is a [2+2] cycloaddition reaction, a [3+2] cycloaddition reaction, or a [4+2] cycloaddition reaction.

22. The process of claim 21, wherein the cycloaddition reaction is a [4+2] cycloaddition reaction.

23. The process of claim 22, wherein the second reactant is a 1,3-diene and the [4+2] cycloaddition reaction is a Diels-Alder reaction.

24. The process of claim 23, wherein the second reactant is a nucleophile containing a pi bond, a lone pair-bearing heteroatom, or a negative charge.

25. The process of claim 24, wherein the second reactant is an aromatic or heteroaromatic compound, and the reaction is an alkylation reaction.

26. The process of claim 25, wherein:
Q is phenyl substituted with zero to 2 nonhydrogen substituents selected from the group consisting of $C_1$-$C_{12}$ alkyl, $C_1$-$C_{12}$ alkoxy, and halo;
$R^{11}$ is selected from the group consisting of hydrogen, $C_1$-$C_{12}$ alkyl, $C_1$-$C_{12}$ alkenyl, $C_5$-$C_{20}$ aryl, and $C_5$-$C_{20}$ aralkyl; and
X is $CR^{13}$.

27. The process of claim 26, wherein $R^{13}$ is -$L^1$-Nu: wherein $L_1$ is a hydrocarbylene, substituted hydrocarbylene, heteroatom-containing hydrocarbylene, or substituted heteroatom-containing hydrocarbylene linker with 2 to 6 atoms in the linker backbone, and Nu: is a nucleophilic group capable of addition to an unsaturated bond.

28. The process of claim 27, wherein Nu: is selected from the group consisting of secondary amino, hydroxyl, and sulfhydryl.

29. A process for catalyzing a reaction between an α,β-unsaturated ketone and a second reactant by lowering the energy level of the lowest unoccupied molecular orbital (LUMO) of the ketone, comprising: contacting an α,β-unsaturated ketone with the second reactant in the presence of the catalyst of claim 9, wherein the second reactant is capable of reacting with the ketone by virtue of the lowered LUMO of the ketone in the presence of the catalyst, and further wherein the second reactant has the structure of formula (IV)

(IV)

wherein:
$R^{11}$ is selected from the group consisting of hydrogen, $C_1$-$C_{30}$ hydrocarbyl, substituted $C_1$-$C_{30}$ hydrocarbyl, heteroatom-containing $C_1$-$C_{30}$ hydrocarbyl, and substituted $C_1$-$C_{30}$ heteroatom-containing hydrocarbyl;
Q is a five- or six-membered aromatic ring containing zero to 3 heteroatoms selected from N, O and S and zero to 4 nonhydrogen substituents, wherein any two adjacent nonhydrogen substituents may together form an additional $C_5$-$C_{30}$ aryl, substituted $C_5$-$C_{30}$ aryl, $C_5$-$C_{30}$ heteroaryl, or substituted $C_5$-$C_{30}$ heteroaryl substituent; and
X is N or $CR^{13}$ wherein $R^{13}$ is hydrogen, $C_1$-$C_{30}$ hydrocarbyl, substituted $C_1$-$C_{30}$ hydrocarbyl, heteroatom-containing $C_{1-C30}$ hydrocarbyl, or substituted heteroatom-containing $C_1$-$C_{30}$ hydrocarbyl.

* * * * *

UNITED STATES PATENT AND TRADEMARK OFFICE
CERTIFICATE OF CORRECTION

PATENT NO. : 7,592,463 B2 Page 1 of 1
APPLICATION NO. : 10/313744
DATED : September 22, 2009
INVENTOR(S) : MacMillan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1057 days.

Signed and Sealed this

Twenty-first Day of September, 2010

David J. Kappos
*Director of the United States Patent and Trademark Office*